United States Patent
Hickle et al.

(10) Patent No.: US 10,720,239 B2
(45) Date of Patent: *Jul. 21, 2020

(54) COMPUTER-ASSISTED PATIENT NAVIGATION AND INFORMATION SYSTEMS AND METHODS

(71) Applicant: Forge Laboratories, LLC, Lubbock, TX (US)

(72) Inventors: Randall S. Hickle, Lubbock, TX (US); Christopher K. Allen, Shallowater, TX (US); Jason Paul Derouen, Dripping Springs, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 16/662,305

(22) Filed: Oct. 24, 2019

(65) Prior Publication Data
US 2020/0098472 A1 Mar. 26, 2020

Related U.S. Application Data

(63) Continuation of application No. 15/548,694, filed as application No. PCT/US2016/017132 on Feb. 9, 2016, now Pat. No. 10,489,554.

(60) Provisional application No. 62/113,937, filed on Feb. 9, 2015.

(51) Int. Cl.
| | |
|---|---|
| H04M 3/51 | (2006.01) |
| G16H 10/60 | (2018.01) |
| A61B 5/00 | (2006.01) |
| G16H 50/20 | (2018.01) |
| G16H 40/63 | (2018.01) |
| G16H 40/20 | (2018.01) |
| G06Q 50/22 | (2018.01) |
| G06Q 10/10 | (2012.01) |
| A61B 5/021 | (2006.01) |
| H04M 3/523 | (2006.01) |
| A61B 5/145 | (2006.01) |
| A61B 5/024 | (2006.01) |

(52) U.S. Cl.
CPC .......... *G16H 40/63* (2018.01); *A61B 5/0022* (2013.01); *A61B 5/021* (2013.01); *A61B 5/746* (2013.01); *A61B 5/747* (2013.01); *A61B 5/7465* (2013.01); *G06Q 10/10* (2013.01); *G06Q 50/22* (2013.01); *G16H 10/60* (2018.01); *G16H 40/20* (2018.01); *H04M 3/5183* (2013.01); *H04M 3/5232* (2013.01); *A61B 5/024* (2013.01); *A61B 5/14532* (2013.01); *A61B 5/14542* (2013.01); *G16H 50/20* (2018.01)

(58) Field of Classification Search
CPC ............. H04M 3/5183; H04M 3/5116; H04M 3/5232; H04M 3/5166
USPC ... 379/265.1, 265.11, 265.12, 265.05, 266.1, 379/266.08, 265.13
See application file for complete search history.

(56) References Cited

U.S. PATENT DOCUMENTS

2008/0004904 A1* 1/2008 Tran ..................... A61B 5/0006
705/2

* cited by examiner

*Primary Examiner* — Thjuan K Addy
(74) *Attorney, Agent, or Firm* — Sarah Hegi Simpson

(57) ABSTRACT

A computer-assisted patient navigational communication system for receiving electronic and oral communications from a patient, scanning data to determine the medical needs of the patient, and displaying relevant information to appropriate medical personnel who can immediately advise the patient of the most appropriate source of medical assistance relating to the patient's identified symptoms.

20 Claims, 11 Drawing Sheets

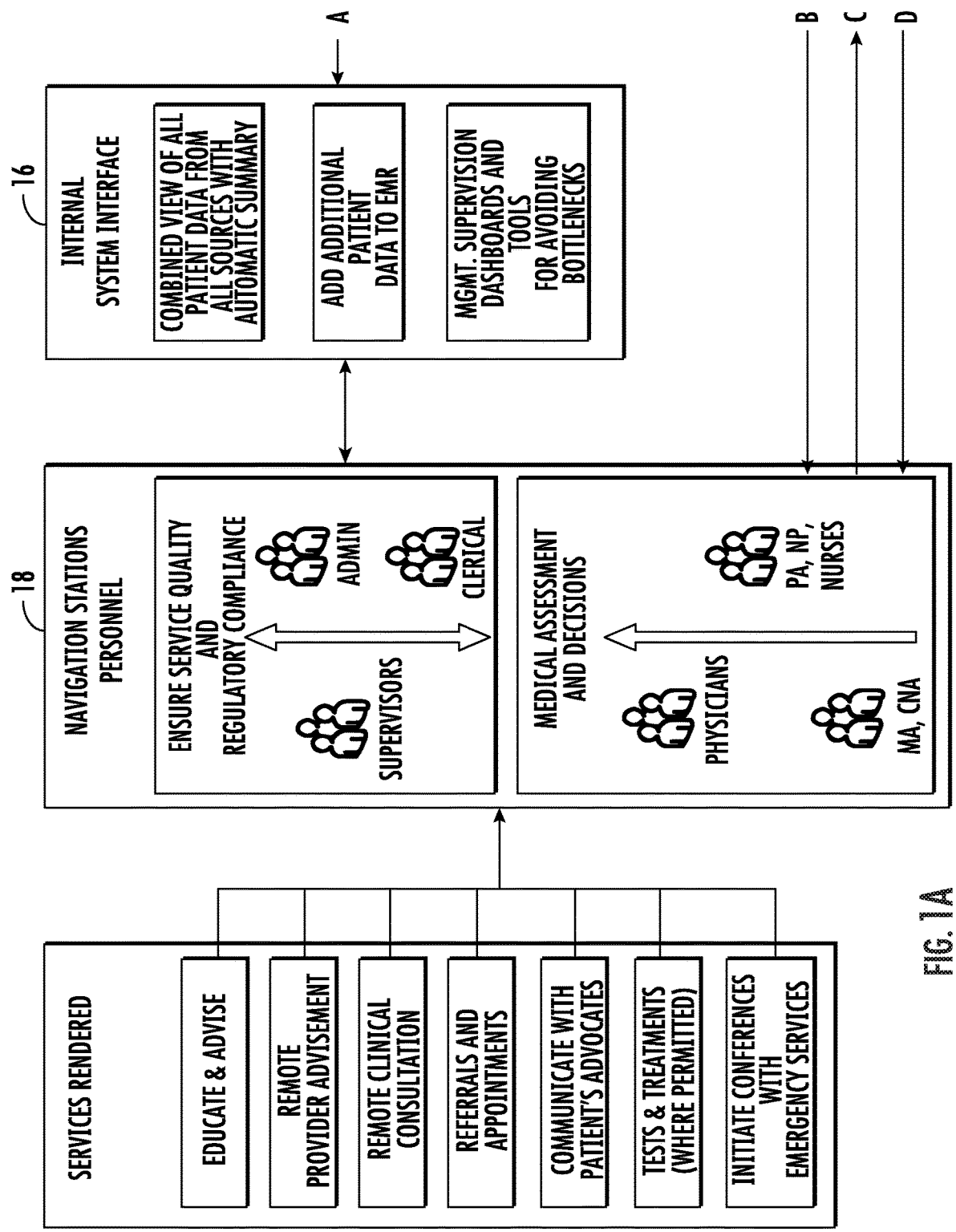

COMPUTER-ASSISTED PATIENT NAVIGATION AND INFORMATION SYSTEMS AND METHODS

CROSS-REFERENCE TO RELATED APPLICATIONS

This application is a continuation application of U.S. application Ser. No. 15/548,694 filed on Aug. 3, 2017, which is a U.S. National Phase under 35 U.S.C. § 371 of International Application PCT/US2016/017132 filed on Feb. 9, 2016, which claims priority to U.S. Provisional Application No. 62/113,937 filed on Feb. 9, 2015, the disclosures of which are incorporated herein by reference. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

COPYRIGHT NOTICE

This application contains material that is subject to copyright protection. Such material may be reproduced exactly as it appears in Patent and Trademark Office patent files or records. The copyright owner otherwise reserves all rights to such material.

FIELD

This application relates to a technology-enabled service with a navigation system for efficiently engaging the patient in the therapeutic paradigm for obtaining appropriate medical care for an existing condition. The patient is provided assistance for efficient navigation through the myriad levels of health care to the appropriate level and provider. Such navigation extends from supervised self-care to proper use of emergency rooms, specialists, hospitals, home health providers, and ancillary service providers to include imaging, laboratory, pharmacy, and therapies such as physical therapy, speech therapy, psychotherapy, and others. Finally, the inventions of this application can also extend to the services of 1) assessment, 2) diagnosis, 3) tests and treatment, 4) education, 5) engagement, 6) monitoring, and 7) management of a patient's health care and his/her wellbeing.

BACKGROUND

A most perplexing problem to a person suffering from pain or having symptoms of a health problem is identification of a proper, immediate source of medical help. With chest pains, does the person rush to an emergency care facility only to learn of temporary indigestion? Does the person with an apparent rash call his family physician, obtain an appointment and later learn that he needs an allergy specialist? Does a person who notices a dark black discoloration on his arm and concludes that it is identical to a melanoma image on the Google web site immediately rush to a dermatologist—only to later learn of a brown spider bite?

Health problems are perplexing, nerve racking and often result in time and dollar costs for unnecessary, expensive emergency room visits, wait times accompanied by anxiety for appointments with physicians or nurse practitioners, and further delays accompanied by more anxiety while waiting for laboratory tests, imaging services, radiologist interpretations, etc.

A related problem is ineffective use of preventive medicine and wellness programs. No one seems willing to pay for monitoring services that early detect changes in physiological factors such as glucose, hemoglobin A1C, blood pressure, aberrant heartbeats, low oxygen saturation, inflammatory markers suggesting arteries at risk for plaque rupture, etc. Indeed, patients and other payers seem to respond to needs for preventive monitoring only after incidents have required costly medical appointments and physician advices. Similarly, individuals commonly delay learning of how to cope with, among others, diabetes, COPD, cancer, smoking, and obesity until adverse complications force consideration of such matters, and even then, such information may be difficult to timely obtain.

There is no known integrated and existing answer to the patient's problems of navigating through the sourcing of medical care providers, effective use of preventive medicine, and educational systems in our medical establishment. Moreover, the current system of providing medical services in this country prohibits the rational development and delivery of a highly efficient, safe, and effective therapeutic paradigm for assessment, diagnosis, treatment, education, engagement, monitoring, and management. Such a rational delivery system should provide a reliable patient navigation system, an effective preventive medicine program, and informative educational curricula. Delivery of this improved health care system should be provided on mobile platforms that comport with modern patient expectations.

A primary reason for the lack of solutions to these problems is the lack of payment for such services and the lack of any potential profitability. In our health system, costs are reimbursed only for medical services that have been coded and submitted for payment to the Medicaid or Medicare payer or the insurance company or the third party payer. Moreover, individuals are reluctant to pay for oral or text advices that are devoid of face-to-face services. And persons will not pay for preventive medicine or informative programs until they recognize the need which often does not arise until adverse health conditions and resulting complications occur. Solutions to these challenges would be a significant advancement in the art.

SUMMARY

In spite of a lack of known profitability, high investment, high direct and indirect costs, the assignee of this application has invested hundreds of thousands of dollars in the conception and development of a patient navigation system (sometimes referred to herein as "Grace Clinic Online" or "GCO," which are trademarks of the Applicant or its affiliate but used herein for ease of reference to such system) for online delivery of a defined therapeutic paradigm that includes patient navigation to the proper medical provider, preventive medicine and information systems. Surprisingly, during the development of the system, market segments have been identified for which substantial time and cost savings can be quantified and for which there is evidence to suggest emerging demand. Accordingly, systems described in this application will provide quantifiable cost and time savings which may lead to sufficient reimbursement to support a durable provision of the herein described technology-enabled services. For example, Managed Care Organizations (MCO) that receive contracts for managing Medicaid and/or Medicare patient populations for the states find it saves dollars when patients are directed to proper medical providers rather than unilaterally seeking unnecessary, high cost, emergency room care. Too, their costs are also significantly reduced by avoidance of hospital stays, and even unnecessary physician appointments. Similarly, MCO's costs may be significantly reduced when a patient with a chronic illness is timely directed to proper medical care when his physiological data is monitored, when the patient's problem is identified and the therapeutic paradigm applied prior to the cost of an ambulance, a trip to the emergency room, and/or a difficult-to-manage escalation in the cascade of care. Significantly, some embodiments of the inventions of this application also include low cost capability to enable physicians, their offices as well as clinics and hospitals to manage Medicare patients with chronic conditions without face-to-face consultations. Indeed, some embodiments of the inventions of this application include an Electronic Health Record (EHR) and/or Electronic Medical Record (EMR) which enables an exchange of information between the physician and the patient, and the physician or staff is available to the patient around the clock. Finally, programs directed to better engagement of patients in their own self-care and wellness will benefit patients of MCOs, particularly with the technology-enabled service described herein that provides clinical supervision of the patient's self-care. Significantly, the systems of this application successfully integrate all of these functions.

In addition to MCOs, the benefits of the present inventions will immediately be recognized by county, federal, and state prison systems in which expensive guard trips to specialists such as cardiologists may be minimized, prescriptions for probiotics may avoid trips to the gastroenterologists, etc. A low cost, online navigational tool providing a technology-enabled service for assessment, diagnosis, treatment, education, engagement, monitoring, and management will improve access and quality while lowering the cost of tax supported medical care to patients including those receiving benefits from Medicaid, Medicare, Veterans Health Services, and governmental employees, in addition to patients in nursing homes, and prisons. Patients paying for their own care and those receiving employee benefits, along with insurance companies and benefit plan administrators, will also recognize the benefits of the inventions disclosed herein.

The present disclosure is premised upon a system having several primary components. Preferably, they include one or more computer servers having: 1) a system interface to receive external physiological data and question responses of the patient from sources such as a medical device (e.g., blood pressure monitor or glucose meter) communicating with a mobile handset such as a cellphone, a medical kiosk, medical diagnostic devices, at home medical devices such as integrated systems provided by Honeywell and other providers, and devices sold at local pharmacies, diagnostic information from similar devices and diagnostic medical devices at a prison facility, a nursing home, or a rehabilitation center, data from laboratories and radiologists, etc., and to store such data into an Electronic Medical Record (EMR) of the members or subscribers of an organization; 2) an enablement unit containing the system EMR database, said enablement unit being programmed to scan the EMR upon request from navigation station personnel and/or upon fixed time intervals, or in response to a triggering event (which may be temporal) or trend, to search for an abnormality of physiological factors for each patient, and to route an identified need of the patient to the most appropriate response, which may be an automated response such as an inquiry as to whether the patient took their blood pressure medicine or an automated request for the patient to repeat their blood sugar measurement, or if indicated, routing of the patient's condition to medical personnel of the navigation stations; 3) an internal system visual interface enabling medical personnel of a navigation station to view the patient's data such as age, sex, health history, physiological conditions from the updated EMR including present symptoms, images, etc., and 4) a navigation station having inbound and outbound oral and digital communication facilities for permitting automated patient engagement as well as interactions with medical personnel such as nurses, nurse assistants, physician assistants and physicians to communicate with the patient, to further obtain information from the patient and to navigate the patient in need of medical help to the most appropriate source of medical provisions. Engagement of the patient in supervised self-care at the nonclinical site through automated interactions with the system (e.g., "Your blood pressure is higher than usual [or appears to be trending upward]; have you taken your blood pressure medications today [or according to the prescribed schedule]?" or "Your blood sugar is low, please recheck it immediately") provides the earliest possible identification and intervention opportunities to improve health, reduce the requirement for personnel staffing, and to reduce costly escalations in care. Such sources may include the entire spectrum of sources, i.e., from status quo to escalation of monitoring and therapeutic intervention at the current site of care, to initiation of emergency treatment and possible emergency transport to an escalated site of care. Such navigation provisions may also include acquisition of new data such as laboratory tests at the point of care or at a laboratory and/or imaging services, medical treatment, or referrals to physicians, telemedicine consultations as well as recommendations for education, self-help, and advices. Finally, such provisions may include not only navigation, but a direct communication, or alert to the patient as well as an exchange of information between the patient and caregivers (nurse assistants and/or primary care physicians) in the navigation station or outside the station. Alternatively, the navigation station may alert the patient's PCP (Primary Care Physician) and facilitate a communication directly between the patient and the patient's PCP.

Realizing that trained medical personnel may have both direct oral telephone communications with a patient in anguish and immediate access to the patient's EMR and incoming data through devices such as remote medical devices, tablets, and smartphones, Applicant has developed a navigation and communication system that may substantially reduce the cost of medical care for various organizations responsible for the health care costs of their members, employees, policy holders, and associated persons such as, for example, state government employees, prisons, nursing homes, corporations and business entities with substantial employees and insurance companies, such as Blue Cross Blue Shield™ and others. Accordingly, various embodiments described herein may:

1) provide timely, accurate, cost saving, navigational guidance to individuals as to the most appropriate health care provider for the individual's condition;

2) obtain access in digital form to all of the available patient health data of associated individuals, including prior claims data, together with current data from kiosk, at-home monitors, manually entered patient data, orally entered patient data, pictures of patient data or physical findings, telemedicine data, data from physiological devices having direct connectivity or wireless communication such as BlueTooth, Wi-Fi Cellular Data, USB to PC or other connectivity, and Microsoft HealthVault™, for example, and/or interface with and store new data in the EMR of a member, employee, prisoner, etc.;

3) analyze updated EMR on a call basis and on a time interval basis to identify abnormalities in physiological factors and route abnormal data to appropriate navigation to automated algorithms and other machine systems and, as indicated, to trained medical personnel to respond;

4) provide a visual interface (and oral interface) with a summary of the updated EMR to trained medical personnel of the navigation stations for oral and data inbound and outbound communications with the individual (which may include, for example, videophone communication applications such as FaceTime™) to guide said individual to the most appropriate self-care responses or health care provider for the existing conditions of the patient;

5) provide inbound and outbound audio and video and data connections to the individual for further evaluating the health condition of the patient and needs for a health care provider, formulate advice, communicate it clearly, and simultaneously make arrangements for implementing said advice through referrals, appointments, lab tests, imaging, home health visits, prescriptions, emergency room and/or ambulance services, as patient conditions and capabilities dictate appropriateness, etc.;

6) provide for the assessment, diagnosis, tests and treatments, education, engagement, monitoring and management of patient wellness and health, particularly where patients with chronic diseases can be well served by continuous and/or repetitive monitoring of physiological conditions by a physician or his staff around the clock; and 7) communicate with both the patient and his PCP with regards to alerts and abnormalities of the patient's health condition, to provide reminders to both the patient and to the PCP as to the need for physiological data readings and needed inputs into the system and, where appropriate, enable the PCP to access the patient's portal and review his EMR data.

In some embodiments, a computer assisted navigational communication system for immediate determination of a remotely monitored medical patient's needs and for guidance of the patient to the proper medical provider responsive to the patient's symptoms may include: an external system interface configured for receiving patient data, including physiological data and historical medical data, pertaining to the patient from one or more of the following sources: a kiosk with physiological diagnostic equipment; home health monitors with communication connections; facility equipment of prisons, nursing homes, and rehab centers; various employer institutions; consulting physicians; laboratories; and imaging centers; and formatting said patient data in a prescribed format to form EMR data; an enablement system configured for analyzing the EMR data, identifying an abnormality, and transferring information pertaining to the abnormality to navigation personnel associated with a navigation station of the system having credentials suitable to direct the patient to an appropriate medical care provider; an internal system interface configured for providing a combined view of the EMR data to the navigation personnel; and a navigation station configured for inbound and outbound oral and data communications between or among two or more of the patient, receptionist, nurse, physician assistant, physician, and other medical providers including one or more of the following: pharmacy, lab, imaging facilities, family and specialist physicians, emergency rooms, hospitals, ambulance services, and rehabilitation services.

In some embodiments, a low cost method for efficiently navigating a patient to the appropriate medical provider for the purpose of avoiding unnecessary costs of facilities such as emergency rooms when appropriate may include: providing members of an organization with a member ID and password for communicating their physiological data via voice and data communications to a navigation system; receiving the physiological data and placing same in an EMR for each respective member; scanning the EMR to identify one or more abnormalities of the physiological data; displaying the EMR upon a visual display and alerting a navigation station that the EMR is being displayed; and communicating through electronic and oral communications between the navigation station and the relevant member for whom the one or more abnormalities were identified to direct that member to the most appropriate medical service provider for such member's health condition.

In some embodiments, a low cost system for providing medical services to a remote patient may include: (a) a system call center configured for communications between a medical service provider and the patient; (b) the call center having access to the patient's Electronic Medical Record; (c) the call center having computer facilities configured for receiving physiological data from the patient through one or more of the following modes: fax, videophone, medical devices connected to the internet, photos of interfaces; (d) the computer facilities having one or more interfaces configured to immediately display the physiological data of the patient and the Electronic Medical Record; and (e) the call center having medical professionals available to immediately review the physiological data and the Electronic Medical Record through a computer interface, and to simultaneously communicate with the patient to directly obtain information to enable the medical service provider to render one or more of the following services: assessment, diagnosis, treatment, education, engagement, monitoring, and managing the patient's condition.

In some embodiments, a low cost system may be provided for accurately communicating physiological data from a remote patient to a medical service provider at a call center for assessment, diagnosis, or treatment of the patient's medical condition. The call center may be configured for receiving a dual tone multi-frequency sound and for displaying information representative of the dual tone multi-frequency sound on a visual interface to enable the medical service provider to assess, diagnose or treat the patient. The call center may include an interactive voice response system configured for receiving a dual tone multi-frequency sound representative of the physiological data and placing the physiological data in memory for analysis. Such low cost system may include: (a) a physiological monitor configured for monitoring a physiological condition of the patient and a means for communicating physiological data concerning the patient from the monitor to a dongle; (b) a dongle configured for receiving the physiological data from the monitor and converting the physiological data into a dual tone multi-frequency sound adapted for transmission to the call center; and (c) a phone configured for receiving the dual tone multi-frequency sound from the dongle and transmitting the dual tone multi-frequency sound to the call center.

BRIEF DESCRIPTION OF THE DRAWINGS

The manner in which the above functionalities are obtained is described in the following detailed description and the drawings, in which:

FIGS. 1A and 1B are a block diagram depicting system functionality and information exchange therein of an embodiment of the present inventions.

DETAILED DESCRIPTION

Figure 1B:
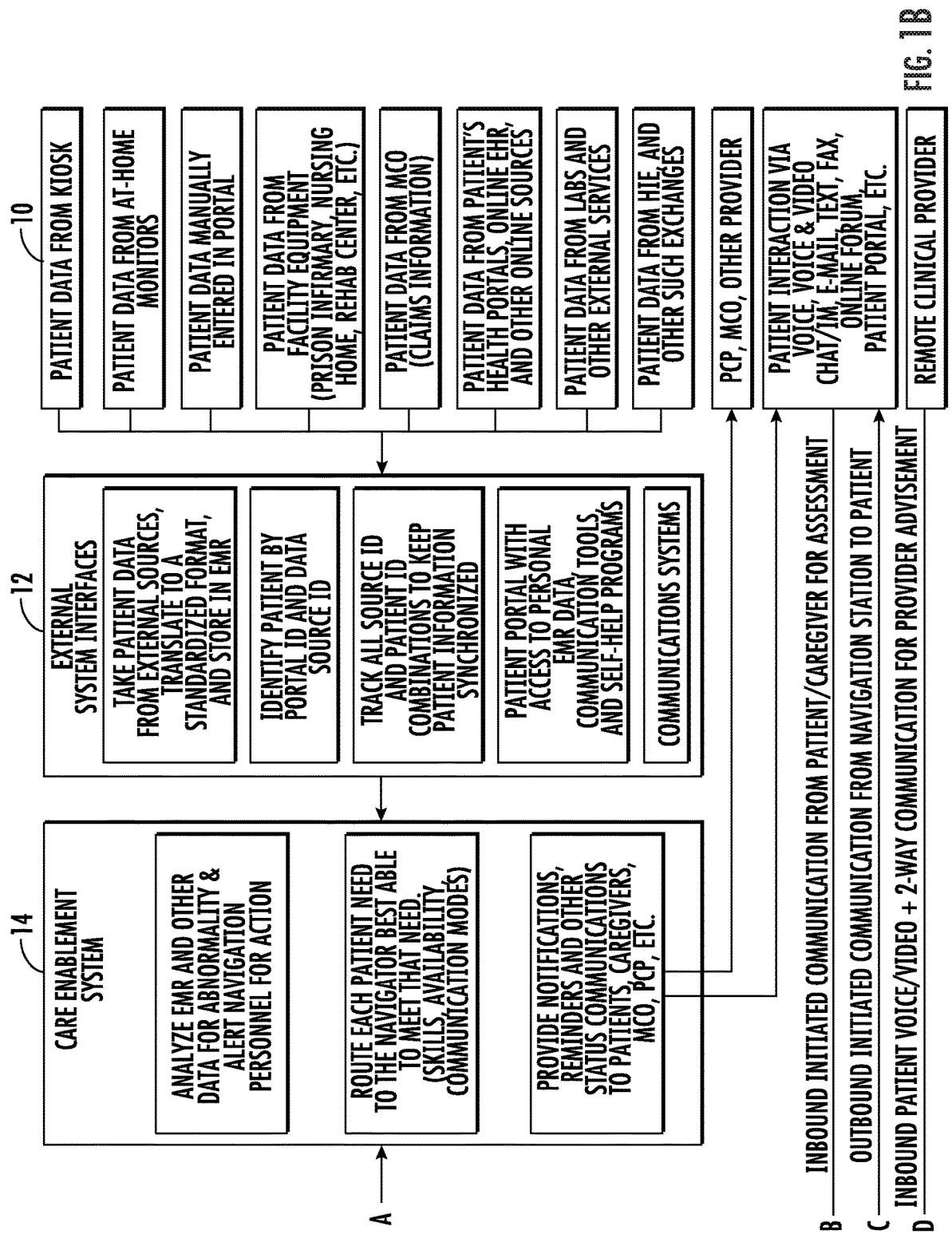

As illustrated in the right hand column of FIG. 1B, Applicant's system may receive patient physiological data from sources that include kiosks having glucose monitors, ECG devices, blood pressure cuffs, oxygen saturation devices, temperature monitors, respiratory rate monitors, cardiac output and stroke volume monitors, and the like. Similarly, at home monitors may provide the same or similar data. Such information may be transmitted via Wi-Fi, Blue tooth or other wireless communication capabilities of the monitors and devices, e.g., from USB ports incorporated into the devices and connected to personal computers or tablets having internet or wireless access, etc. Another source is the patient who reads the output of the devices and transmits them, e.g., via a desktop computer or smartphone, to the patient's portal on the system. Other sources of information for the system include diagnostic patient data from facilities such as nursing homes, prison infirmaries, rehabilitation centers, prior claims from a MCO, data from laboratories, and external databases, etc. Similar information may be accessed from third party health records, which may include sources such as Microsoft's HealthVault™, health information exchanges, fitness portals, and other services. Finally, another external source is the patient's audio, video, and data communication through a telephone and/or other communication devices. Indeed, oral and video communications enabling the patient to speak directly to the medical personnel using the system may be preferred as significant information is often best solicited from astute questions of the medical personnel as well as the voice and visual demeanor of the patient.

As noted earlier, one benefit of some embodiments of the inventions of this application is the immediate provision of the most appropriate service and navigation instructions to the patient. Exemplary outputs or navigation provisions from the system are illustrated in the left hand column (Services Rendered) of FIG. 1A. Where the symptoms and data from the patient indicate no serious health problem, the patient may be merely provided with advice, or alternatively directed to an education and self-care video regarding a specific health problem. Such videos may extend from the need for patient review of conditions such as weight loss, smoking cessation, minor complications with a pregnancy, etc., to highly sophisticated explanations for self-care of complex and co-morbid conditions, such as by way of example chronic pulmonary disease causally associated with cardiac electrical rhythm aberrancy, and when monitored cardiac rhythm aberrancy worsens, how to check pulmonary status as, by example, with spirometry and pulse oximetry, and then escalate pulmonary therapy such as by administration of home oxygen or by self-administration of breathing treatments by physician-prescribed medication protocols. With ongoing monitoring, patient education and active engagement, and supervision (herein, "supervised self-care"), highly effective and cost effective care can be safely administered even in home settings, whereas such sophisticated care would previously only be delivered in a high cost setting such as an intensive care unit. When the symptoms and data from the patient indicate serious health problems, such as slurred speech and inability to control an arm or appendage, ambulances may be ordered, the emergency room advised of the possibility of an incoming stroke victim, etc. Between these provisions of mere advice and emergency procedures is a host of other services, including remote clinical consultation, ordering of blood and urine tests, compliance reminders, requests for monitor calibration, referrals to family physicians and/or specialists, etc.

The present systems may provide immediate analysis of the input data from the devices and the patient, display of the data and analysis to medical personnel, and immediate advice as to the most appropriate medical provider and service available based on the patient's actual needs. To accomplish these results, the systems and methods of FIGS. 1A-1B include an interface management system (10) having an external interface (12) for receiving data from the sources mentioned earlier and for translating that data into a standard format and storing it in the EMR of the system. For identification of the patient, the MCO that seeks to reduce its health care costs may provide its members with an ID for entry of their data into the system. In the alternative, employers, prisons, and others who contract for navigational care may have available kiosks with physiological monitors available for obtaining the information and immediately transmitting same to the system. Too, the patient can obtain data from his home monitors and transmit same with his smartphone, tablet, or other computer device or manually enter the data through a patient portal on the interface (12) of the system (10).

As well known in the art, computer programs for interfacing the incoming data into the system interface 12 are commercially available or readily created, and persons skilled in the art can use these programs as well as modifications thereof to receive, format, and store the incoming data in the system EMR. In addition, each patient is preferably provided with a patient portal to access his/her EMR, to obtain access to self-help and education programs pertinent to his/her health.

The system EMR is part of the care enablement system (14) which is herein described as a technology-enabled service delivering supervised self-care and navigational support. Preferably, it comprises a data record stored in a database with various fields for each data type, e.g., blood pressure, glucose reading, oxygen saturation, etc. The function of this enablement unit is to search and/or scan the EMR for abnormalities upon receipt of the data or, alternatively, at timed intervals, or in response to defined events in the system. When found, an alert is transmitted to the navigation personnel (18) for action. This scanning can be performed upon receipt of the data and storage in EMR. In addition to scanning for abnormality, the enablement system (14) can be programmed to search for changes or emerging trends in the individual's data. For example, if systolic readings were normally 110 and suddenly, a new reading as high as 180 were received, the enablement system can be programmed to direct the navigational personnel to make an outbound communication to the patient to inquire of the potential cause for the change. Such early detection and preventive medicine may well avoid costly appointments, hospital stays, etc.

Upon determination of abnormalities or receipt of patient concerns and data analysis, the enablement system (14) may be programmed to first verify the abnormality is correct by rechecking the information or following other automated algorithms based on the incoming data and then if indicated route the inbound call or text problem of the patient, or the alert of abnormality, to the most appropriate medical person to navigate the patient to the most appropriate health care provider of the navigation station (18). To achieve this result, personnel qualifications such as credentials, areas of special knowledge, languages, and other evaluated skills of the medical care personnel in the navigation station (18) are input and may be associated with various symptoms, chronic diseases, communication barriers and other factors. For example, an abnormality alert for a trend of increasing glucose readings in a diabetic patient might be routed to a nurse with deep experience evaluating and counseling chronic diabetes patients, whereas a call from a patient with stuttering and loss of movement might be routed to a physician MD or a physician's assistant with a focus on emergency care. Algorithms for first verifying the correctness of the incoming abnormal data and then weighting the various factors and associating certain personnel with specific conditions and symptoms may be used.

Simultaneous with the routing of a specific patient problem to a specific person on the navigation station (18), the EMR of the patient and all related data may be placed upon the internal system interface (16) to display the EMR and related data to navigation personnel. In addition, the pertinent navigation personnel may accept the inbound call or electronic communication from the patient and begin a further clinical protocol discourse to elicit any additional desired information from the patient. Additional pertinent information received may be added by the navigation personnel to the patient's EMR. After evaluating the information received, the navigation personnel may begin delivery of the appropriate option from the available "services rendered," which may include directing the patient to the most appropriate health care provider. Such may include directing the patient to any of the sources of the left column of FIG. 1A. Alternatively, it may be appropriate for the medical personnel of the navigation station 18 to directly provide the needed medical advice, or alternatively to bring the PCP into the discussion.

Another benefit of these systems is the ability to monitor patient data continuously or at time intervals as needed. For example, many patients will be requested by their health care providers to submit physiological data pertaining to their health condition periodically, e.g., weekly, or several times a day. For more serious conditions, physiological data such as ECG and O2Sat may be submitted substantially continuously. The care enablement system (14) may be programmed to scan and search for abnormalities on a regular time interval basis or upon events such as immediately upon receiving new data for the patient. In the event an adverse or abnormal condition is detected, the unit may direct the appropriate navigation station personnel to clinically evaluate the data and take appropriate action. Alternatively, notifications of problems, reminders to provide data, status communications, and the like may be directly provided to the patient and/or to the patient's PCP.

It is also contemplated, as reflected in FIGS. 1A-1B, that data from the patient may be accepted, converted to the EMR of the enablement system (14), and analyzed on a 24 hour basis. Similarly, inbound calls or electronic communications from the patient may be made at any time of the day or night. As an alternative, the navigation system can be used by a PCP or his staff who, by accessing the EMR of the system, can review, directly contact, and manage chronically ill patients on a 24 hour basis. Alternatively, the PCP can delegate this function to a physician or nurse assistant of the navigation station (18).

As appreciated by persons skilled in the art, numerous modifications may easily be made to the systems and methods described above. One beneficial modification is to add a navigation analysis system to insure quality and timely response by the personnel of the navigation station (18). For example, if the number of inbound calls exceeds a prescribed limit, e.g., 4 calls per navigation person, additional navigators may be added immediately. Similarly, if the wait time for any patient exceeds a prescribed limit, e.g., five minutes, additional navigators may be added immediately. Similarly, additional sources of medical providers can always be added to the left column of identified providers, and different interfaces can be added to accommodate inbound data from other devices or additional sources. Finally, special criteria may be added in the form of additional scan parameters for searching the EMR's to identify specific health conditions and problems. Accordingly, all such additions and modifications are contemplated as within the scope of the inventions set forth in the following claims. If the patient has a health condition that requires daily monitoring and/or input of information, the system may be programmed to receive such data, and if not received, the care enablement system (14) may be programmed to send an instruction to the most appropriate navigation station 18, or alternatively, to send a reminder directly to the patient member to provide the required data, for example, his glucose reading or his blood pressure.

Figure 2:
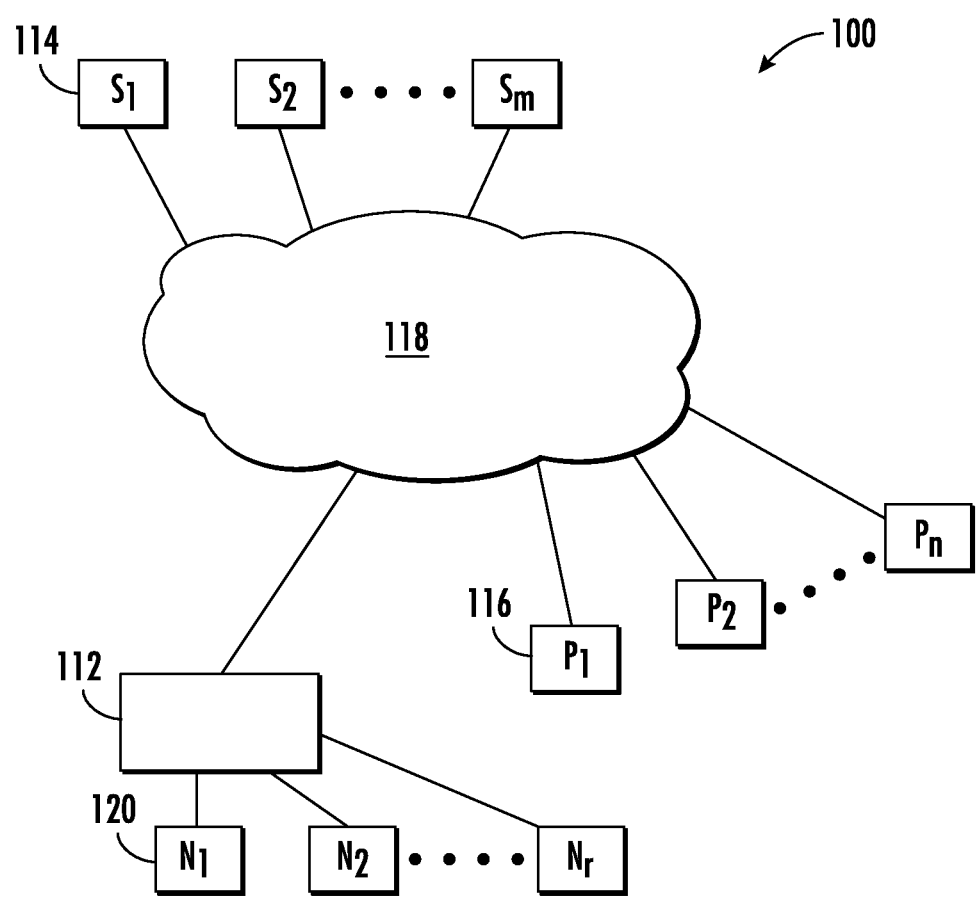
FIG. 2 is a schematic diagram illustrating another embodiment of a health care navigation system as described herein.

Referring to FIG. 2, in some embodiments, a supervised health care patient navigation system 100 may have a central computer 112 in communication with a plurality of service provider computers 114 associated with a respective plurality of health care service providers S1 . . . Sm (e.g., doctors, therapists, labs, and the like) and a plurality of patient computers 116 associated with a respective plurality of patients P1 . . . Pn via one or more networks 118, e.g., the Internet, telephone, and/or other suitable communication networks. A plurality of health care navigators N1 . . . Nr (e.g., doctors, nurses, physician assistants, and the like) may provide input to and receive output from central computer 112 either directly or through respective navigator computers 120. Communication between central computer 112 and navigator computers 120 may also be through the one or more networks 118. Central computer 112 may serve as a secure central repository of health care data concerning the plurality of patients P1 ... Pn as well as a communication hub for the various persons described herein. Health care navigators N1 ... Nr may communicate with patients P1 ... Pn and service providers S1 ... Sm to coordinate health care services for the patients through network 118, which may include any of a number of different types of communication, such as regular telephone communication, text messages, electronic mail, videoconferencing, or other suitable forms of communication, some or all of which may occur substantially simultaneously or sequentially.

Figure 3:
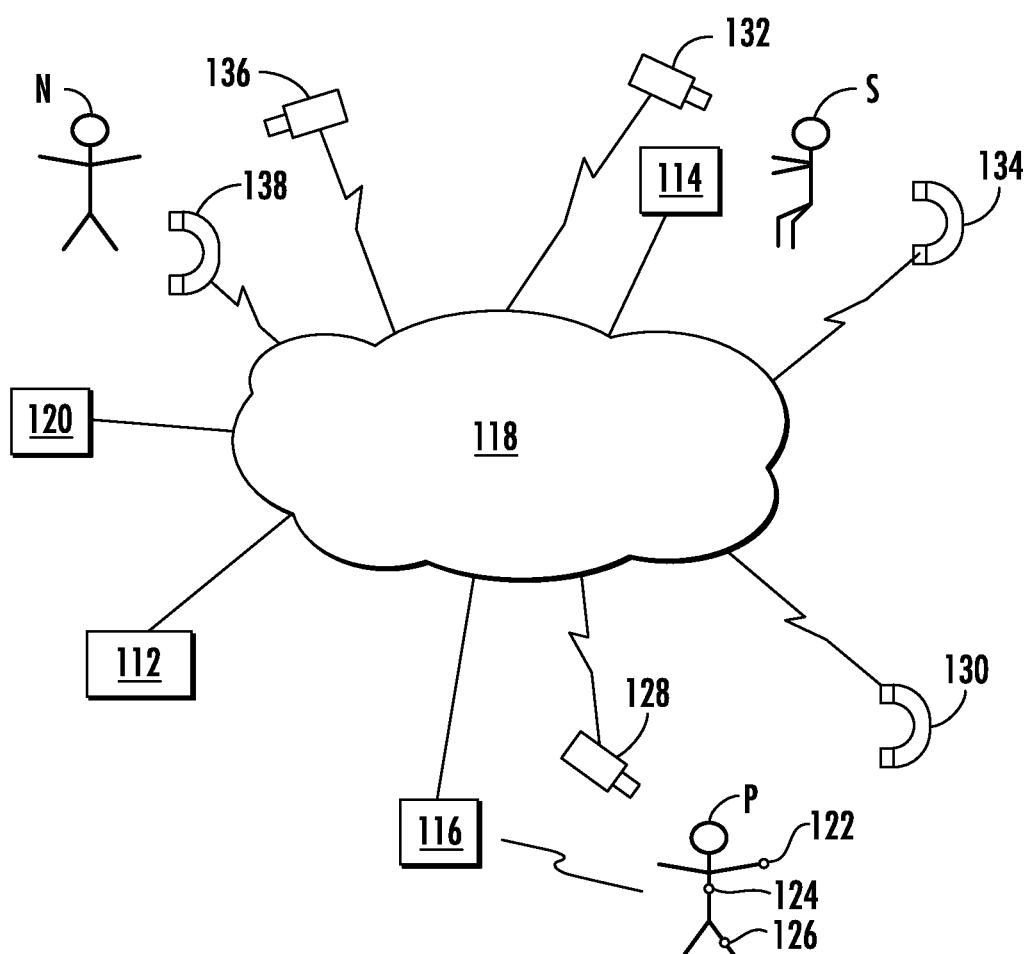
FIG. 3 is a schematic diagram further illustrating a portion of the system of FIG. 2.

Referring to FIG. 3, in some embodiments, each patient P may have one or more sensors 122-126 (sometimes referred to herein as monitor devices) configured to measure one or more physical characteristics, e.g., weight, heart rate, blood pressure, blood glucose level, blood oxygen level, ECG signals, or any other measurable physical characteristic of a patient. Sensors 122-126 may be attached to or embedded in the patient P or they may be separate from the patient P. In some embodiments, sensors 122-126 may be worn by a patient periodically or substantially continuously. In some embodiments, sensors 122-126 may be part of a kiosk in which a patient P may sit, stand, or lie down. Sensors 122-126 may send data representative of the one or more physical characteristics of the patient P to patient computer 116, which may send such data to central computer 112 via the one or more networks 118. Such sending of patient data may be manual, automatic, or in response to a command or request, and such sending of patient data may be substantially continuous, periodic, or discrete. Subject to appropriate permissions, each service provider S may access such patient data on central computer 112 pertaining to each patient P to whom service provider S is providing a health care service through a service provider computer 114 and the one or more networks 118. Such patient data may be "pushed" to each service provider computer 114 or navigator computer 120 by central computer 112 based on certain criteria, or such patient data may be "pulled" from central computer 112 by each service provider computer 114 or navigator computer 120 upon request. Each patient P may also access his or her patient data on central computer 112 via patient computer 116 and the one or more networks 118.

Figure 4:
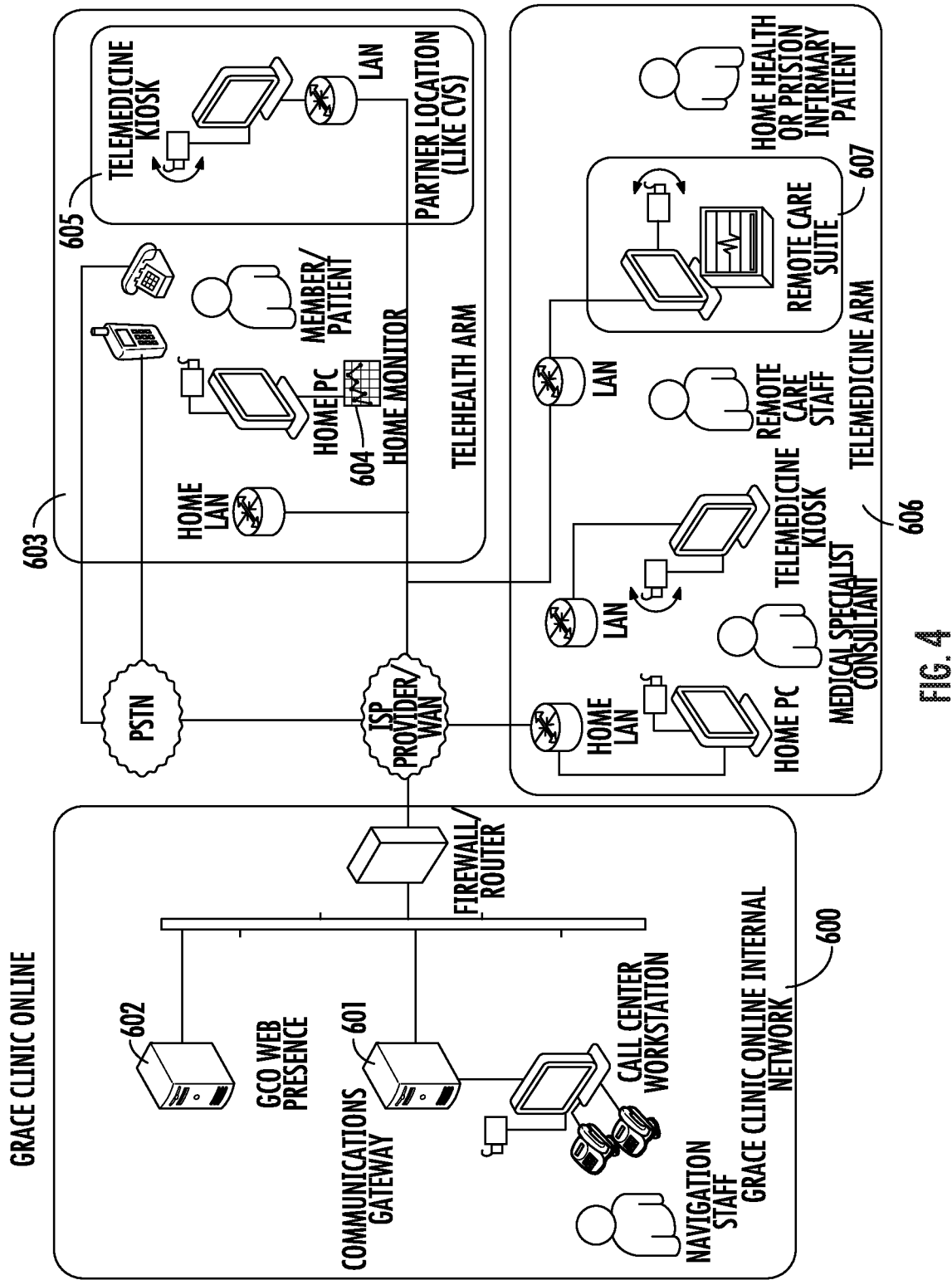
FIG. 4 is another schematic diagram illustrating yet another embodiment of a health care navigation system as described herein.

Still referring to FIG. 3, each patient P may also have a video camera 128 (e.g., a web cam in communication with the one or more networks 118 via patient computer 116) and a microphone and speaker 130 (e.g., a telephone) in communication with the one or more networks 118, which may also be via patient computer 116. Similarly, each service provider S may also have a video camera 132 (e.g., a web cam in communication with the one or more networks 118 via service provider computer 114) and a microphone and speaker 134 (e.g., a telephone) in communication with the one or more networks 118, which may also be via service provider computer 114. Likewise, each navigator N may also have a video camera 136 (e.g., a web cam in communication with the one or more networks 118 via navigator computer 120) and a microphone and speaker 138 (e.g., a telephone) in communication with the one or more networks 118, which may also be via navigator computer 120. Each patient computer 116, service provider computer 114, and navigator computer 120 may have a display configured for displaying video data and patient data. As persons of ordinary skill in the art will appreciate, using this system, a navigator N may direct a patient P to the most appropriate service provider S based on the patient's needs, and such service provider S may provide health care services to a remote patient P in a virtual environment in which some or all of the service provider S, the patient P, and the navigator N may see and hear each other in substantially real-time communications (hereafter, a virtual patient visit). Of course, for hearing impaired or visually impaired patients or service providers, alternative I/O devices may be utilized in order to provide the appropriate forms of communication for such persons. Before, during, and after a virtual patient visit, the service provider S and the patient P, as well as the navigator N, may have access to the patient's data (EMR) on central computer 112 via the one or more networks 118 to help facilitate the rendering of health care services to the patient using up-to-date patient data. Another possible arrangement of such a system is shown in FIG. 4.

A health care navigator N, who may also have access to patient data on central computer 112, may help facilitate the rendering of appropriate in person or remote health care services to each patient P by one or more appropriate service providers S, some or none of whom may be present in the same location. An actual or virtual patient visit may involve one or more service providers S. For example, based on the particular patient data, a health care navigator N may facilitate a virtual patient visit among the patient P, a primary care physician, and a specialist physician. If applicable, a pharmacist or rehabilitation specialist, for example, may also join the virtual patient visit. When a patient contacts such a health care navigator N, the health care navigator N may effectively conduct triage, and the most appropriate health care services may be provided to the patient P based on the patient's actual needs as reflected by up-to-date patient data. This method reduces the cost of providing health care services, improves the quality of care, and enables remote patients to receive health care services from specialists and other health care providers whom the patients otherwise would be unable to access.

Each patient P may also access a variety of health education materials (e.g., articles, videos, presentations, and the like) provided on central computer 112 via a patient computer 116 and the one or more networks 118. Such health education materials may be tailored for each patient P based on the patient data stored on central computer 112. For example, a patient P who suffers from diabetes and high blood pressure may be granted access to educational materials for those specific diseases, but such patient may or may not also have access to educational materials that pertain to other diseases or conditions. Based on the patient data stored on central computer 112, each patient P may be directed to the health education materials that are most beneficial to the particular patient. In this manner, each patient P may be empowered to assume greater responsibility and accountability for his or her health care, thereby reducing the overall cost of health care and making it more efficient, yet providing appropriate supervision by qualified medical personnel to enhance the likelihood of positive outcomes for each patient.

In some embodiments, the health education materials may comprise videos in which professional actors, rather than physicians, for example, convey the health education information. Professional actors may communicate the relevant health education information to patients in a manner that is much more engaging and understandable for patients, which improves the likelihood that the patients will understand and act on the information, thereby improving patient outcomes.

Based on the patient data stored on central computer 112, central computer 112 may also prompt a patient P to take certain actions with respect to his or her health care by sending messages to patient computer 116. For example, if a patient's treatment plan calls for collecting a certain measurement by a certain date, central computer 112 may prompt the patient P on or in advance of such date to take the measurement and input the measurement data into patient computer 116 for transmission to central computer 112 via the one or more networks 118. Additionally, if the patient misses a particular deadline, central computer 112 may prompt the patient P with a reminder concerning the same. In some embodiments, central computer 112 may send one or more alert messages to a patient if the patient data on central computer 112 indicates an emergency or other adverse condition exists or is about to occur so that the patient may take corrective action, which may be indicated in the alert messages. In some embodiments, appropriate action items pertaining to a particular patient may be included in or with the educational materials that are tailored for that particular patient. For example, if a patient suffers from asthma, an educational article on asthma may include a link that takes the patient to his or her specifically tailored action item plan for asthma. A navigator may help facilitate such actions as well.

In some embodiments, central computer 112 may be configured to grant various rewards to patients based on their compliance with their particular health and wellness plans. For example, if a patient P meets all or a certain percentage of his or her action items (e.g., reviewing certain health education materials, sending in certain measurements, or the like), such patient may receive a cash award, a discount on certain goods or services, a virtual medal, one or more points toward a reward program, a better insurance rate, a lower deductible, or some other suitable reward.

In some embodiments, central computer 112 may be configured to provide an online portal for each patient P who subscribes to the service. From a home page, each patient may access a variety of resources, including one or more health and wellness plans tailored for each patient. For example, a given patient may have a smoking cessation plan, a diabetes management plan, and a cholesterol management plan. Each health or wellness plan may have one or more programs that are also tailored for each patient. A patient's portal may also include various monitors, alerts, health risks, action items, information, and announcements. In some embodiments, the patient data for each patient on central computer 112 may include a continuity of care document having a standard data format for ease of use by multiple service providers S.

In some embodiments, central computer 112 may be configured to coordinate telephone communication, video-conferencing, and online communication among health care service providers S1 . . . Sm, patients P1 . . . Pn, and health care navigators N1 . . . Nr in a manner that entails low enough cost and efficiencies of scale to achieve synergistic results that could not be achieved otherwise. For example, with the aggregate patient data that may be collected by central computer 112, data analytics may be employed by central computer 112 to identify various social determinants of health, such as educational focus, career planning, reading activity, partner selection, parenting skills, mentorship, physical fitness, substance abuse, physical or emotional abuse, and the like, and appropriately tailored education and action items may be provided to each patient in view of those analytics and the patient's particular health data. One aspect of the systems and methods described herein that may yield such beneficial results is that each patient P is empowered, via the online information portal, to assume greater responsibility and risk for his or her health care, along with receiving appropriate incentives for such assumption, thereby consuming fewer health care resources. Another aspect is that each service in the overall system of health care services may be performed by the lowest cost resource initiated first with machine logic then progressing to a tier of personnel who are qualified for the particular service. Optimal utilization of this online healthcare system may produce substantial improvement in health and reduction in healthcare costs; however, achieving these results may require timely patient interaction, including the input of requested information and compliance with system recommendations. In some embodiments, an explicit goal of the system herein taught may be that rewards and withholding of rewards may be allocated according to the performance of each patient. One of the preferred embodiments for the rewards may be allocation of mobile minutes, data, internet access, handset upgrades, and other desired attributes of cellphone services as a reward for high performing patients. High performing patients may rely on the machine logic of the system; lower performing patients may rely more on the clinical staff which will cost much more. Even so, the system will triage the patient according to the required level of care. For example, in some embodiments, the health care navigator N role may be fulfilled by properly educated nurses or physician assistants rather than physicians, and a lower cost but qualified specialist may be used rather than a higher cost specialist, when appropriate, based at least in part on the aggregate patient data collected by central computer 112.

FIG. 4 shows a more detailed embodiment of the GCO system described in FIG. 3. The GCO internal network 600 shows a possible network topology that may meet the needs of GCO Navigation Staff. The call center workstation may provide telephony for communicating with patients, remote care staff, and medical specialists. An attached or embedded camera may provide means for video conferencing with patients, medical specialists, and/or remote care staff The communications gateway (such as a private branch exchange) may provide this rich suite of communication options. The GCO application server 602 may provide work flow control for the GCO Navigation Staff as well as web presence to the patient for interaction with his or her medical data. The patient side network topology 603 may be as simple as a cell phone for upload of information via voice, keypad input, or a mobile application. For those circumstances where the patient has a remote monitor 604, for example a blood pressure meter or a blood glucose meter, the GCO embodiment may support various options to upload the data via a home PC, cell phone application, and voice or keypad entry via a phone, for example. Additionally, a deployed telemedicine kiosk 605 may provide the monitor suite and connectivity to gather data from the patient and allow communication to the Navigation Staff. In some instances, if the telemedicine kiosk 605 is not normally in the same location as the patient, the patient may need to travel to the location of the telemedicine kiosk 605. The final piece of this GCO embodiment may support the remote staff and consultants who provide medical services as shown at 606. On the medical specialist side, a home PC may be suitable for the job, for example, or a specially deployed telemedicine kiosk PC may be desired for a more advanced service level in some instances. On the more advanced side of the application, remote care staff for example a home health care worker or prison infirmary staff, may utilize a specialized remote care suite 607 that may allow for a higher service level. Such a specialized remote care suite 607 may employ FDA approved monitoring devices, for example, for data acquisition from the patient in support of critical care. In addition, remote care suite 607 may employ higher resolution cameras with embedded actuators, for example, supporting remote control for examination purposes.

Figure 5:
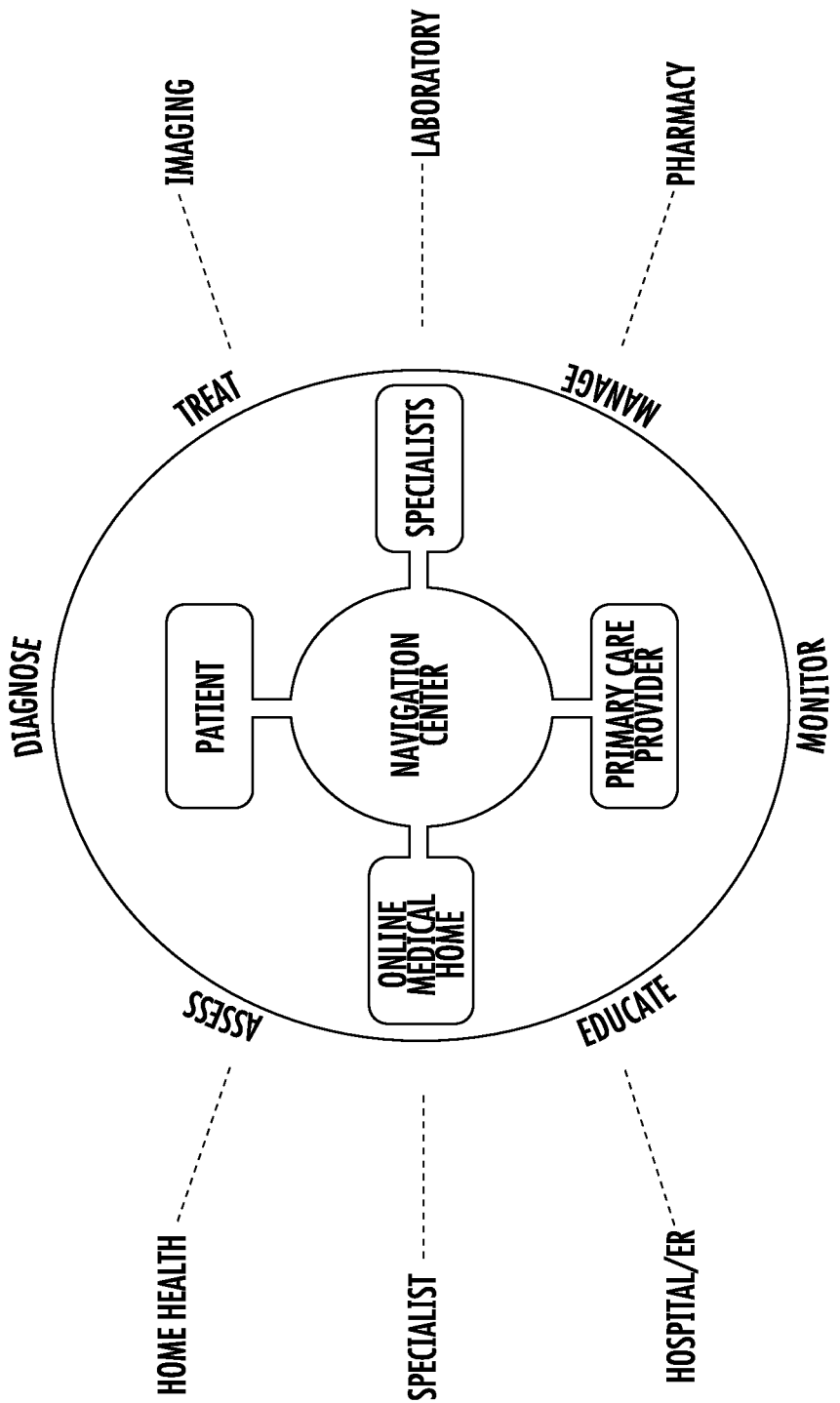
FIG. 5 is another block diagram illustrating various aspects of a health care navigation system as described herein.
Figure 6:
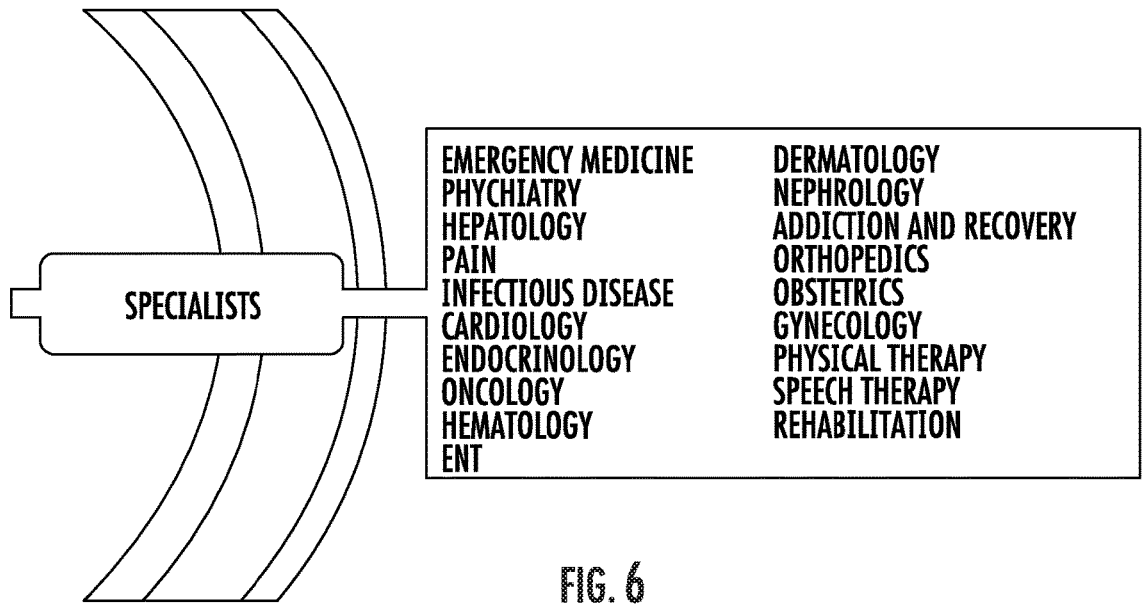
FIG. 6 is a listing of various specialists that may participate in a health care navigation system as described herein.

Referring to FIG. 5, in some embodiments, the foregoing functionality may be implemented in the form of a clinical management organization as shown. The computer assisted navigation station 18 referenced above may take the form of a navigation center with one or more navigators N, which may coordinate health care services for a plurality of patients with the respective PCPs and a variety of specialists, examples of which are illustrated in FIG. 6. The system may be used to assess, diagnose, treat, manage, and monitor the medical conditions of each patient and educate each patient according to his or her specific needs.

Figure 7:
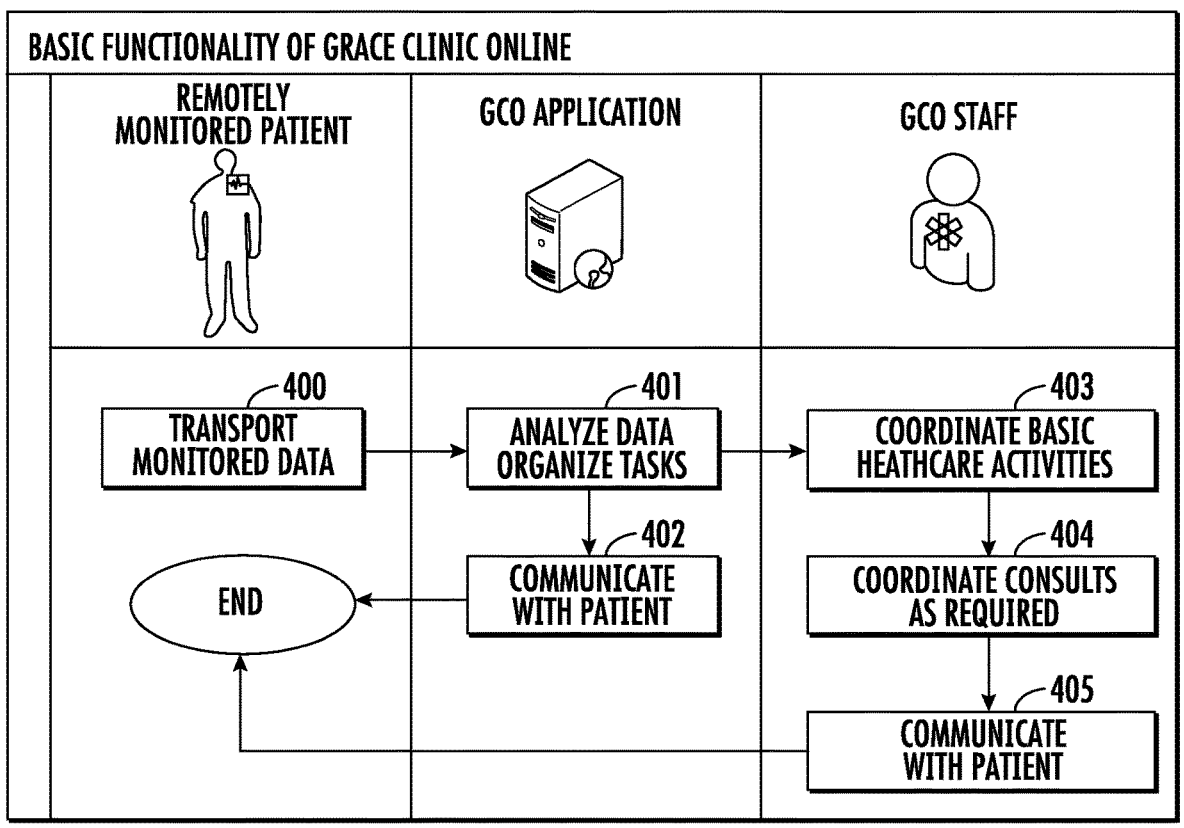
FIG. 7 is a high level schematic diagram illustrating basic functionality and interaction of an embodiment of a health care navigation system as described herein.

FIG. 7 illustrates the high level features of GCO. Typically, the remotely monitored patient must transport healthcare data 400 (e.g., from sensors 122-126 noted above, manual entry, or otherwise) to the GCO Application, which may run on central computer 112 described above, for example. This communication of data 400 may occur in a number of ways that span voice, encoded audible signal, high frequency modulated signals such as modems, file transports such as FTP, and standard Internet transmission protocols, for example. The data 400 may include any information that may be collected directly from the patient, such as a depression scale, or collected from a remotely deployed device like a blood pressure monitor, for example. Additionally, this data may derive from other sources such as Managed Care Organizations, Health Information Exchanges, participating providers' electronic medical records, and peripheral service providers like clinical laboratories, imaging centers, and pharmacies, for example. From there, the GCO Application may analyze the data and organize tasks based on clinical protocols as indicated at 401. At this point, the GCO Application may assign tasks to the GCO Staff (e.g., navigators N discussed above) and/or launch automated processes that communicate with the patient without involving human resources as indicated at 402. In some embodiments, the tasks assigned to the GCO Staff may range into three broad categories. First, the GCO Staff may coordinate basic healthcare needs for a patient as indicated at 403, such as doctor appointments or laboratory tests, for example. Second, the GCO Staff may get external specialists involved for consultation with the patient and GCO Staff as needed as indicated at 404. Third, the GCO Staff may contact the remotely monitored patient directly to provide assistance and medical coaching as shown at 405.

Figure 8:
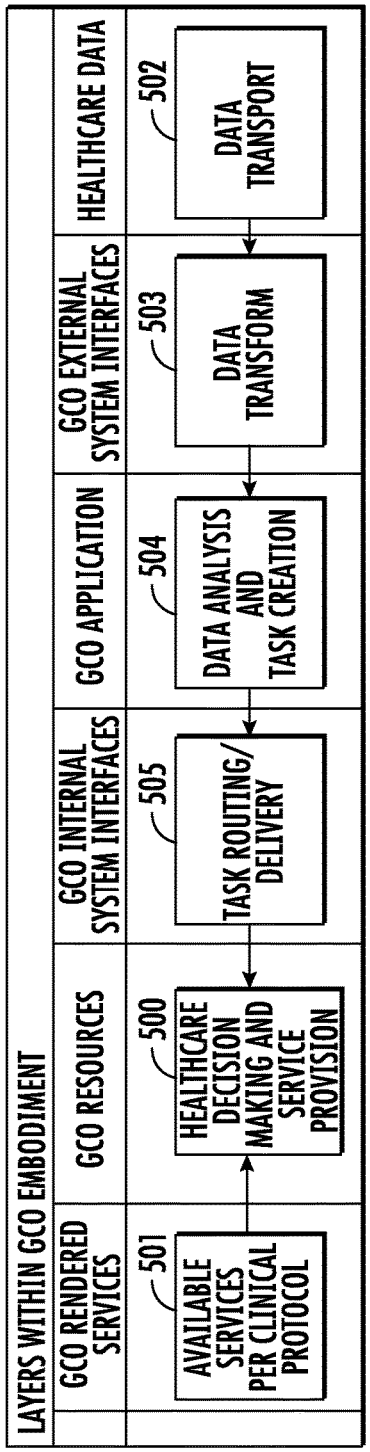
FIG. 8 is a schematic diagram illustrating various layers of an embodiment of a health care navigation system as described herein, showing all workflow focused on the final outcome of service provision.

FIG. 8 illustrates a layered viewpoint of GCO. This figure shows how all the workflow embodiment within each layer ultimately results in the provision of services 501 to the patient as shown at 500. The services may cover a spectrum of healthcare needs covering education, consultation, referrals and appointments, advocacy, and test and treatments. The GCO Resources which provide these services may vary between automated systems such as auto-dialers and web applications (e.g., controlled by the GCO Application on central computer 112) to human resources (e.g., navigators N) such as medical staff, supervisors, and administrators. The supporting foundation of the services is the healthcare data that must be transported as shown at 502 to the internal workings of the GCO system. As explained in connection with FIG. 7, this transport or communication of such healthcare data can occur in a number of ways that span voice, encoded audible signal, high frequency modulated signals such as modems, file transports such as FTP, and standard Internet transmission protocols, for example. The data can derive directly from the patient input or it can be collected from a remotely deployed device like a blood pressure monitor, for example. Additionally, this data may derive from other sources such as Managed Care Organizations (MCOs), Health Information Exchanges (HIEs), participating providers' electronic medical records, and peripheral service providers like clinical laboratories, imaging centers, and pharmacies, for example. The GCO external system interfaces may transform the data as shown at 503 to a format understandable by application logic as necessary. Thereafter, the GCO Application can perform analysis of the data and create tasks as shown at 504 in accordance with the needed actions as determined by the analysis. The GCO internal system interfaces may perform routing and delivery of tasks as shown at 505 to the various GCO Resources, whether human or automated or both, as applicable.

Figure 9:
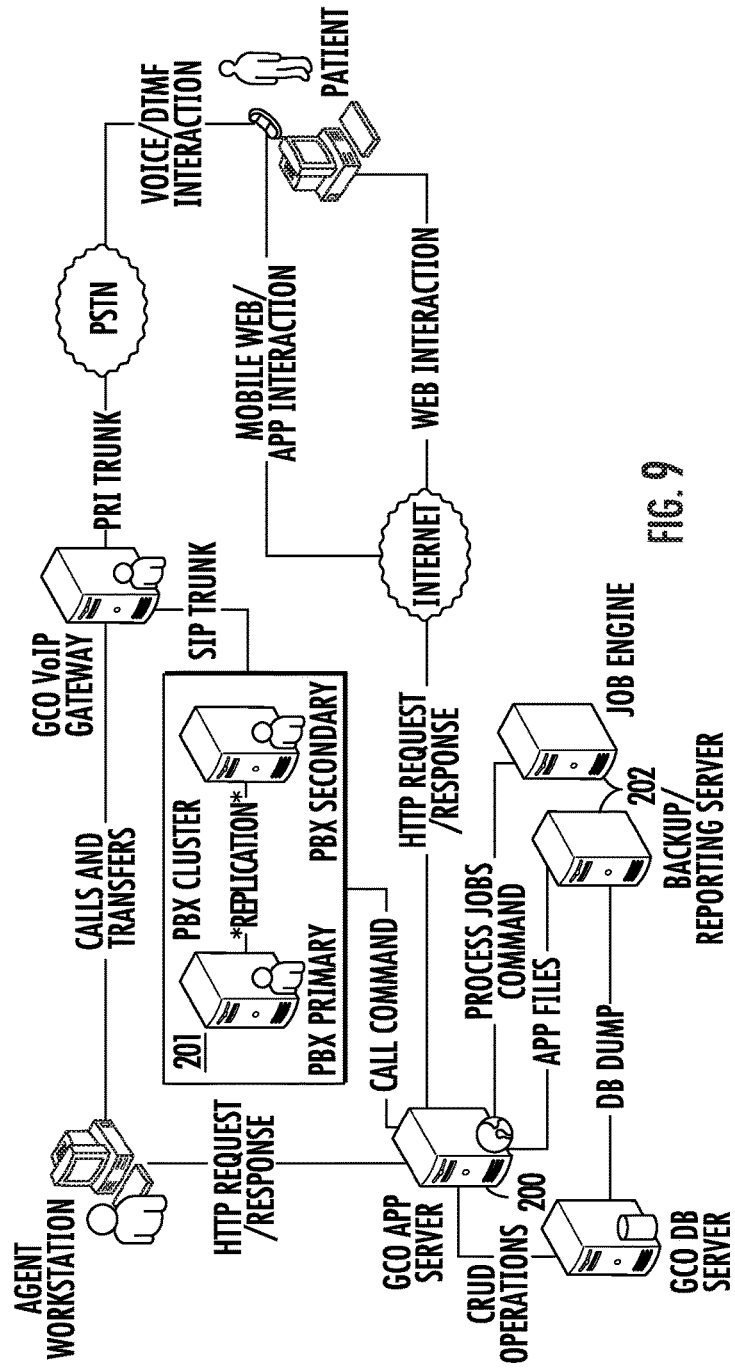
FIG. 9 is a network diagram illustrating a sample configuration of technology that may be used to implement a health care navigation system as described herein.

FIG. 9 illustrates one of many options showing a sample network topology that may be used to implement a GCO embodiment. A GCO App Server 200 coupled with a GCO DB Server may provide the main application logic and data storage needs. The GCO App Server may include a web server that can execute and interpret HTTP requests and responses. This may allow for patient and staff interaction with the GCO system through an Internet browser, for example. A PBX Cluster 201 having primary and secondary machines may provide a fault tolerant implementation of the internal GCO Private Branch Exchange (PBX). The PBX Cluster 201 may execute the outbound and inbound calling campaigns (e.g., telephone communications between or among GCO staff, patients, and other medical service providers) as loaded by the GCO App Server 200. The PBX Cluster 201 may provide the auto-dialer services and interactive voice response trees used to define such calling campaigns. The PBX Cluster 201 may also interpret any Dual Tone Multi Frequency (DTMF) signals, for example, and translate them into meaningful data for transfer to the GCO App Server 200. Additionally, PBX Cluster 201 may interpret voice signals into meaningful commands, which may be passed to GCO App Server 200. In some embodiments, the GCO system may interface with the Public Switched Telephone Network (PSTN) in order to establish a voice channel with a remote patient. The diagram of FIG. 9 shows this communication through a VoIP Gateway device. Peripheral systems, e.g., Backup/Reporting Server and Job Engine 202, may provide supporting activities for the GCO App Server 200. The Backup/Reporting Server may duplicate the production database as well as any application files and folders. The Job Engine may provide for commanding the GCO App Server 200 to execute specific jobs periodically. Additionally, the Job Engine may provide some extra capability regarding data transformation in order to support linking the GCO App Server 200 with external systems.

Figure 10A:
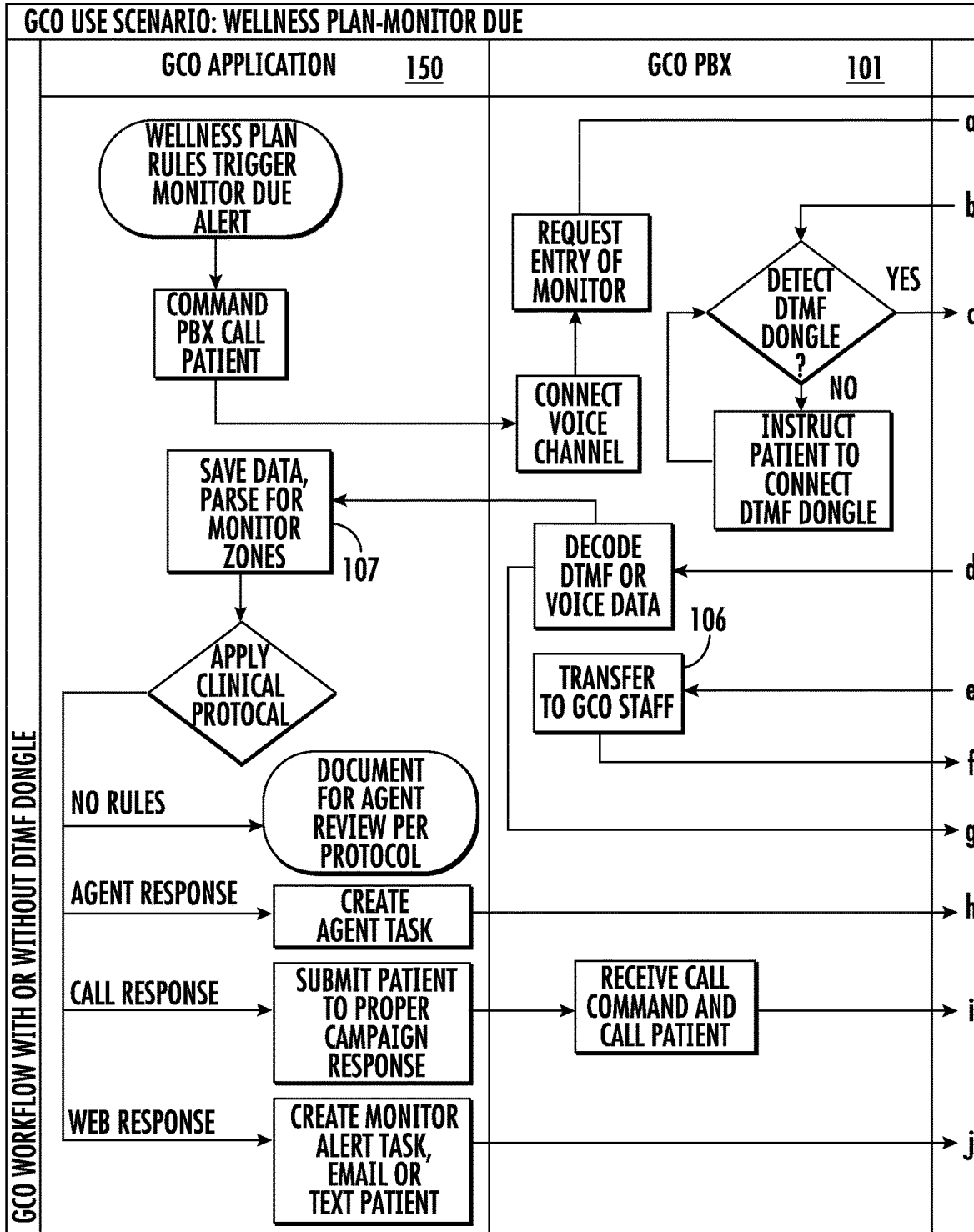
FIGS. 10A and 10B are a process flow diagram illustrating a sample use case scenario showing process flow applied when a monitor entry is due by a remotely monitored person.
Figure 10B:
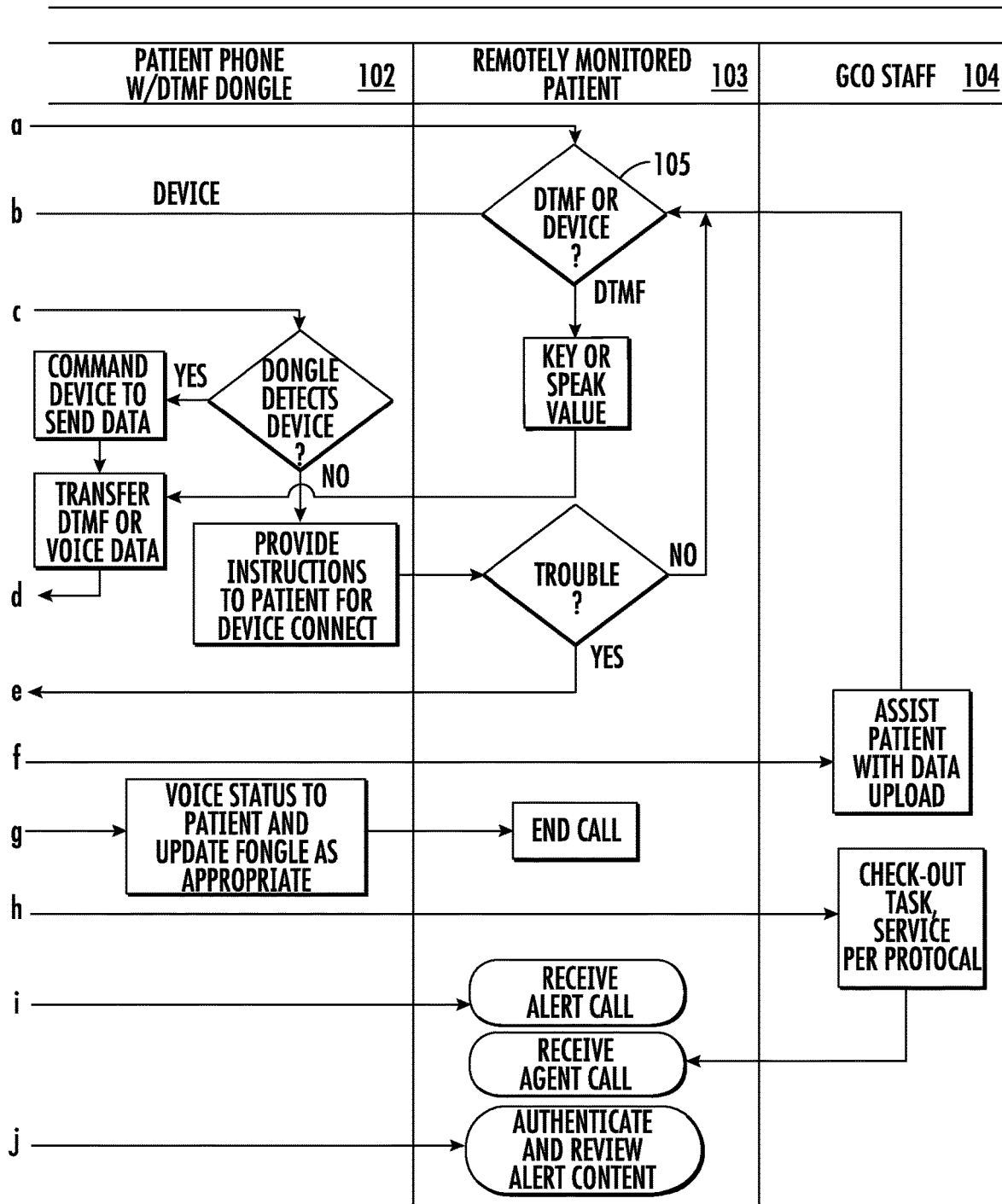

FIGS. 10A-10B illustrate a use case scenario within a GCO embodiment. In the provision of remotely monitoring a patient, the patient may provide periodic updates to GCO regarding the patient's one or more monitored metrics. A monitored metric may be any physical parameter that pertains to the patient's health, such as blood glucose, blood pressure, temperature, weight, or heart rate, for example. FIGS. 10A-10B show the logical sequence that follows a determination by the GCO system that a monitor (e.g., an update to a monitored metric) is due. In some embodiments, this scenario may involve five main components, as illustrated by the five columns of FIGS. 10A-10B. GCO Application 150 may be the principal source of all business logic associated with GCO services, specifically remote monitoring as depicted in FIGS. 10A-10B. GCO PBX 101, or Private Branch Exchange, may be a GCO private telephone network that allows for executing inbound and outbound call campaigns associated with GCO services. FIGS. 10A-10B show two different options for retrieving monitor data from patients: a "DTMF Dongle" or user entry via voice or keypad. The DTMF Dongle may be part of the package Patient Phone w/ DTMF Dongle 102. This DTMF Dongle may be an automated device that can automatically send data collected from a monitor device like a blood glucose meter, for example. This data transmission may be done using a DTMF signal to encode the monitor data and send it over a voice channel established with the PSTN. Of course, there are many other options for retrieving data from a monitor device, such as a photograph of the device screen, smartphone application using data connection via the Internet, voice signal, modem transmission, or any other technology that modulates the analog signal over a voice channel, for example. Though there are many options, the DTMF Dongle embodiment works well because it encodes data in the same manner that a user (e.g., patient or provider) would enter data through the keypad of a phone. In this way, the GCO PBX 101 can service data entry by the user or data entry by the DTMF Dongle. The remotely monitored patient 103 may receive periodic contact from GCO regarding the patient's healthcare state. In this scenario, patient 103 may receive contact from GCO requesting an update of monitor data. Finally, the GCO Staff 104 may provide general coaching and assistance as needed.

Any wellness plan serviced by GCO, such as diabetes management, for example, typically may require data entry of patient metrics pertinent to the specific plan. The logical flow shown in FIGS. 10A-10B concerns a determination that the monitor data for a specific patient is due. This determination may originate from the GCO Application 150 and may trigger a command to the GCO PBX 101 to call the patient 103 and request entry of the monitor data based on a specific outbound call campaign. When the remotely monitored patient 103 answers the phone, he or she may receive a pleasant greeting along with a request to enter the monitor information. At this point (see 105), the patient may do so by speaking the values, taking and transmitting a photograph of the values, keying the values on his or her phone, connecting a hard-wired communications link between the monitor and the phone, or sending the data with the DTMF Dongle 102. If requested, the specific calling campaign may explain to the remotely monitored patient 103 how to use the monitor device to extract this data and how to use the DTMF Dongle 102 if the patient desires to do so. The DTMF Dongle 102 may utilize a means to connect to the monitor device, such as Bluetooth or USB, for example, and extract the monitor device data. Once extracted, the DTMF Dongle 102 may encode the monitor device data as a DTMF signal, which is the same mode the patient may use to send the data if he or she does so with the phone's keypad. If the remotely monitored patient 103 has any trouble with the calling campaign instructions, he or she may request assistance, and the GCO PBX 101 may transfer the patient (see 106) to the next available GCO Staff 104. Here the staff member may provide necessary instruction to get the remotely monitored patient entering data with the DTMF Dongle, phone keypad, or voice, for example. Once GCO PBX 101 receives the data, it may transfer the data to the GCO Application 150, which may parse the monitor data entries for specific zones which may broadly fall into various classifications (see 107). The classifications may depend on the value of the metric but may also depend on values of other metrics as aggregated together. For example, an isolated single systolic blood pressure of 190 may be treated at a low level of priority, but the priority may rise if associated with a series of elevated systolic blood pressures or if associated in the GCO EMR with a patient who had a prior history of a hypertensive hemorrhagic stroke. As another example, Body Mass Index (BMI) is a calculated value based on two metrics: height and weight. Taken on their own, height and weight may not fall into any zones dictating action; however, once the application calculates BMI, its value may fall into various zones dictating response. There may be any number of these zones, such as normal, marginal, warning, or critical, for example. Given the classification, the GCO Application may proceed to apply any clinical protocols attached to the classification. The one or more clinical protocols may result in one or more actions being taken. For example, the actions may include creating a task for GCO Staff 104 to execute a follow-up call with the patient, or it may result in placing the remotely monitored patient 103 within another call campaign that may provide specific information to that patient. As another example of such action, specific content may be packaged for review by the remotely monitored patient 103 on the GCO web site via a mobile phone, tablet, or PC device, for example. Such content may include, for example, an educational video that explains a specific healthcare concept pertinent to that specific patient based on the collected monitor data.

Figure 11:
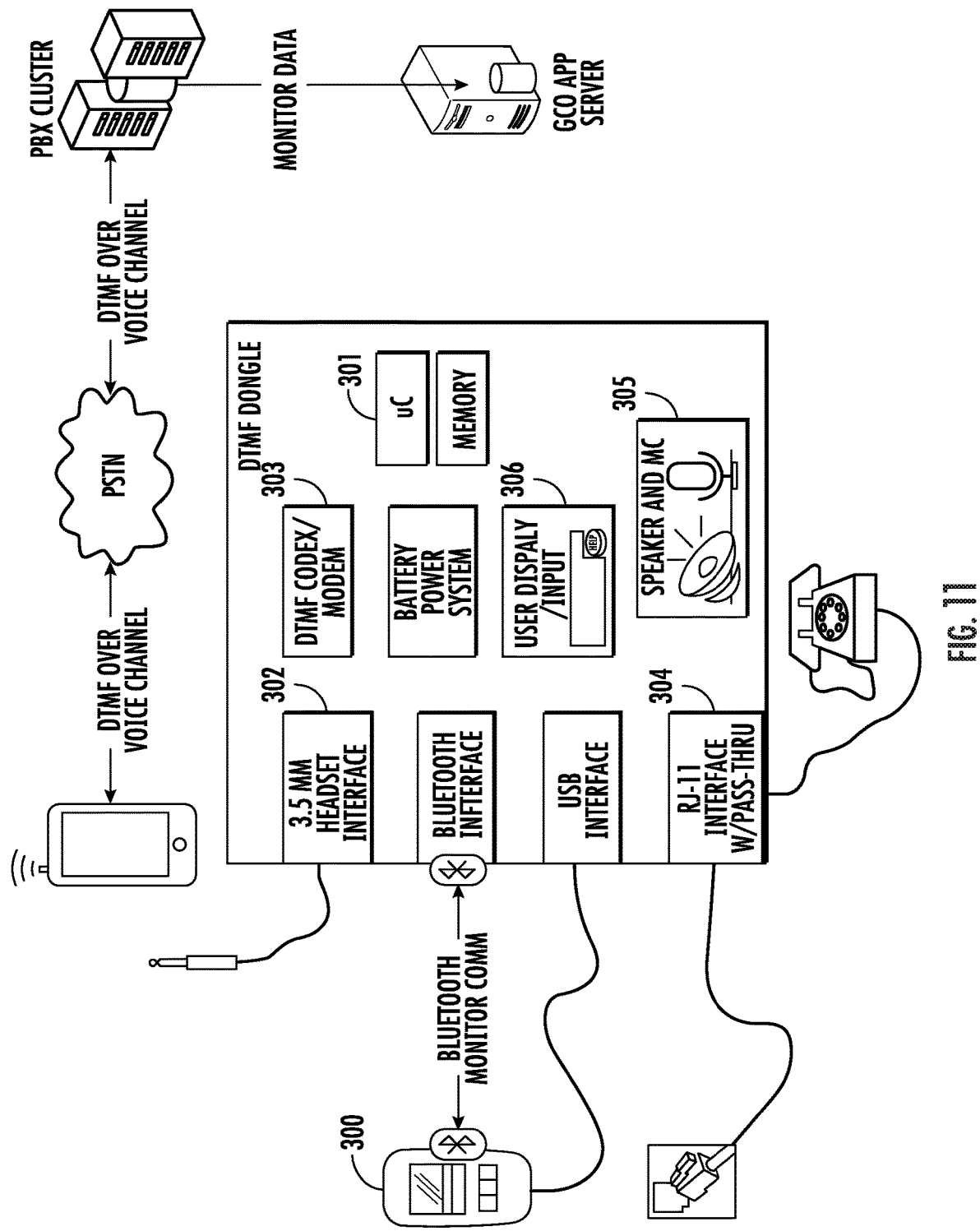
FIG. 11 is a schematic diagram illustrating an embodiment of a DTMF Dongle that allows for data collection from a remote monitor device and sending such data to GCO.

FIG. 11 illustrates a sample embodiment for the DTMF Dongle. The DTMF Dongle embodiment can support any number of means to connect to a remote monitor device, such as a blood glucose meter 300, for example. The communication connection between the DTMF Dongle and the remote monitor device may occur via any suitable means, such as Bluetooth and/or USB, for example. A DTMF Dongle microprocessor 301 and memory may provide all of the required computational logic to run the various subsystems that comprise the DTMF Dongle. In some embodiments, a 3.5 mm headset interface 302 may provide the principal means for connecting to the patient's phone. Using the DTMF Codex/Modem 303 module, the interface may allow for transmission of the DTMF encoded signal representing the monitor device data to the GCO App Server 200. Such transmission may be through the PSTN and PBX Cluster 201 described above. In some embodiments, the foregoing disclosed components of the DTMF Dongle along with the Battery Power System may comprise the core systems required to transmit data over the established voice channel. Given those components, the DTMF Dongle may be made as small and inconspicuous as possible. The other components may allow for extension of the DTMF Dongle feature set. For example, an RJ-11 Interface w/ Pass-thru 304 coupled with the modem side of the DTMF Codex/Modem 303 may allow for direct connection to RJ-11 jacks as typical with established residential telephone lines. A User Display/Input 306 may provide additional guidance to the user when collecting data from a remote monitor device and/or transmitting data to the GCO App Server 200. A Speaker and Mic module 305 may allow the DTMF Dongle to become an integrated calling station. Given this Speaker and Mic module 305, the patient may use the DTMF Dongle as a speaker phone and communicate with the GCO Staff as required and still upload monitor data as well. This integration may allow for filtering the beeps and bops associated with DTMF and modem transmission.

Methods for Retrieval of Biometric Data

Various methods of gathering biometric or physiological data are available and anticipated for the future to be used in implementing a GCO system as described herein. Each method may be employed with various subsets of patient populations based on the requirements of serving each population. Some or all such methods may comply with the Health Insurance Portability and Accountability Act (HIPAA) and other industry standard security requirements, and with FDA, State Medical Board, or any other regulations that may be applicable depending on the specific population and services being rendered.

Self-Reporting: In a self-reporting method, the patient may take a measurement of a physiological quantity using an FDA certified medical device, for example, and observe the result using the provided human interface of that device. The patient may then deliver that measurement data through one or more mechanisms which may be initiated by either the patient or the GCO system. For example, the patient may enter such data:

a. Verbally via any voice communication system directly to a care coordinator, or other designated persons in the navigation center 18, who then may enter the medical data into the GCO electronic system. The information may be conveyed vocally, by TTY, through a translator, or by any other method the patient would normally use for voice communications.
   b. Via telephone to a standard interactive voice response (IVR) system capable of accepting the information via standard DTMF signals entered by the patient on the keypad, or equivalent, on the patient's voice communication device, via speech recognition capable of parsing the information from the patient's input, or via any other methods made available by the IVR system.
   c. Using a software application on a smart-phone, tablet, personal computer, or other device in the patient's possession. The software application may use any method of data entry available to receive the input from the patient. The application may deliver that result either directly to the GCO organization's electronic system, or to a third party entity that then delivers the data to the GCO system.
   d. Through a website, or equivalent remote software portal, where the patient can authenticate his or her identity and report result data from any capable device such as a computer, smart device, or public terminal, for example.
   e. Through a standard fax system by rendering the data in written form and faxing that rendering. The rendered fax image may then be parsed by a standard optical character recognition system and entered into the electronic GCO system, and/or by a human that interprets the rendered image and enters the data into the electronic GCO system.
   f. Through any combination of the foregoing methods or any other methods in which the patient gathers the information from a medical device and reports that data to the GCO organization.

MDDS: In an MDDS method, the patient may take a measurement using an FDA certified medical device, for example, and the result may be observed by another device and/or system classified as an exempt Medical Device Data System (MDDS), or other equivalent FDA exemption, for example. The MDDS may deliver the data through one or more mechanisms to the GCO organization directly or to a third party entity that then delivers the data to the GCO organization. An MDDS method may involve:

a. Reading results from the medical device by:
      i. Connecting to the medical device electronically, such as via USB, Bluetooth, Wi-Fi, Serial, or similarly capable connections that allow the MDDS system to observe the medical device's result; or
      ii. Reading the results from the medical device using the provided human interface of that device in a way approximating the method used by a human. For example, such methods may include using a camera to visually gather information from the device and interpreting the image for the data (e.g., Vital Snap™ available from Validic (Durham, N.C.)), listening to a device with audio feedback components and parsing the sounds for the data, or any other sense interfaces.
   b. Reporting the data back to the GCO organization directly, or through a third party intermediary:
      i. As secured electronic data transported via the Internet, private network, cell network, or any other equivalent digital data transport; or
      ii. Using standard voice communication paths and rendering the data as human speech utilizing a text-to-speech software engine. The resulting synthetic human speech transmission may be received, decoded, redundantly tested for accuracy, and entered into the GCO organization's electronic system by an interactive voice response (IVR) system, and/or by a human representative of the GCO organization; or
      iii. Using standard voice communication paths and rendering the data as encoded sounds. The data may be encoded as standard DTMF tones, other tonal frequency encoding, rhythmic encoding like Morse code, for example, or any other method of encoding data into audible signals. The resulting encoded data may be received, decoded, and entered into the GCO organization's electronic system by a software system capable of decoding the audio.

FDA Certified Medical Device: For some patient populations, an FDA certified medical device that includes delivery of the results data via FDA certified methods may be required.

a. FDA certified medical devices and their data delivery systems may take many forms with many different delivery methods. Some of those certified delivery methods are the same, or similar to, MDDS delivery systems mentioned previously but meet more stringent regulatory standards.
   b. FDA certified systems usually deliver data to a third party certified electronic system. The GCO organization's human agents may then access the data directly through the third party's software interface, and/or automated connections may be made between the third party system and the GCO organization's electronic system.

Passive Systems a. It is anticipated that systems available in the future may collect and deliver data differently from currently available technology.
      i. Future devices and delivery systems may gather continuous data and deliver a pre-processed subset of information as needed, or they may just deliver data at scheduled intervals without requiring discreet conscious action by the remote patient.
      ii. Future control-independent devices may use the same or similar methods of reporting data as previously described.
      iii. Future devices, or current devices with modification, may utilize some new method of transporting the result data to a central system.
   b. The GCO organization's electronic systems may be constructed so that these changes in technical details of transporting information from the patient's medical sensors to the GCO organization's electronic system do not fundamentally change the GCO organization's electronic systems.

As persons of ordinary skill in the art will appreciate, in some embodiments, systems and methods described herein may involve replacing some rote activities within the healthcare arena currently executed by staff with automated processes. For example, such activities may include: (a) providing feedback to the patient based on medical history, which may include but is not limited to blood pressure trends, blood glucose trends, medication list, family history, and appointment history, using feedback routes to the patient via any number of suitable modalities including but not limited to text, email, web application, outbound call campaigns, or any combination thereof, wherein the feedback content may include but is not limited to voice, video, text, slideshows, pictures, or any combination thereof which provides information to the patient specific to his or her current state; and (b) reminding the patient concerning obligations based on their disease state, which reminders may include but are not limited to upcoming appointments, required lab test due, and entry of remote monitor data, for example. In some embodiments, such systems and methods may handle such automated tasks only as directed by approved clinical protocols. In some embodiments, those same protocols may direct inclusion of a medical professional to follow-up with the patient.

In some embodiments, such systems and methods may involve implementing an automated method for gathering remote monitor values from the patient. Examples of remote data acquisition may include, but are not limited to, data entry via voice channels, transmission of a picture of a monitor display, data upload via any network/Internet protocol (HTTP, HTTPS, FTP, FTPS, SFTP, and the like). The transport modes over a voice channel may include, but are not limited to, analog single modulation/demodulation (e.g., the ubiquitous modem or any other scheme encoding data such as Dual Tone Multi Frequency, or DTMF) and voice itself. The remote data acquisition may occur via a remotely established gateway device that serves as an interface to the transport medium. Such gateway device may include, but is not limited to, a commercial product (e.g., cable modem, cell router, and the like), a specifically designed gateway device (such as a DTMF dongle), or the patient's existing gateway infrastructure (e.g., cell phone, tablet, PC, or the like communicating directly to the network medium or running through an established gateway device within the home).

In some embodiments, systems and methods described herein may include providing the patient with medical history, medical record update, and disease state education on demand Such provision may be embodied by access to a web host that provides content to the patient as requested given proper authentication. Such request and response interaction may be initiated by the patient through a mobile application or web application, for example. Such interaction may also occur via a specifically designed device used by the patient.

Persons of ordinary skill in the art will understand that the systems and methods described herein may be implemented via one or more computers, which may have one or more memories programmed with one or more programs on one or more computer readable media. Although only one central computer 112 is shown, two or more such computers may be employed, depending on the needs of the particular application. Among other things, the various components and functionalities illustrated in the Figures and described herein may be implemented on the same computer or different computers and in one or more pieces of software. Any feature described for one embodiment may be used in any other embodiment. Persons of ordinary skill in the art will also understand that various changes may be made to the systems and methods described herein without departing from the scope of the invention. Therefore, the invention is to be construed in accordance with the claims attached hereto and is not to be limited to the embodiments described herein.

Definitions

As used herein, the following terms should be understood to have the indicated meanings, unless the context reveals otherwise.

"Communication" means the transmission of one or more signals from one point to another point. Communication between two objects may be direct, or it may be indirect through one or more intermediate objects. Communication in and among computers, I/O devices and network devices may be accomplished using a variety of protocols. Protocols may include, for example, signaling, error detection and correction, data formatting and address mapping. For example, protocols may be provided according to the seven-layer Open Systems Interconnection model (OSI model), the TCP/IP model, or any other suitable model.

"Comprises" means includes but is not limited to.

"Comprising" means including but not limited to.

"Computer" means any programmable machine capable of executing machine-readable instructions. A computer may include but is not limited to a general purpose computer, mainframe computer, microprocessor, computer server, digital signal processor, personal computer (PC), personal digital assistant (PDA), laptop computer, desktop computer, notebook computer, smartphone (such as Apple's iPhone™, Motorola's Atrix™ 4G, and Research In Motion's Blackberry™ devices, for example), tablet computer, netbook computer, portable computer, portable media player with network communication capabilities (such as Microsoft's Zune HD™ and Apple's iPod Touch™ devices, for example), camera with network communication capability, wearable computer, point of sale device, or a combination thereof. A computer may comprise one or more processors, which may comprise part of a single machine or multiple machines.

"Computer readable medium" means a non-transitory article of manufacture having a capacity for storing one or more computer programs, one or more pieces of data, or a combination thereof. A computer readable medium may include but is not limited to a computer memory, hard disk, memory stick, magnetic tape, floppy disk, optical disk (such as a CD or DVD), zip drive, or combination thereof.

"GUI" means graphical user interface.

"Having" means including but not limited to.

"Interface" means a portion of a computer processing system that serves as a point of interaction between or among two or more other components. An interface may be embodied in hardware, software, firmware, or a combination thereof.

"I/O device" may comprise any hardware that can be used to provide information to and/or receive information from a computer. Exemplary I/O devices may include disk drives, keyboards, video display screens (including GUIs), mouse pointers, joysticks, trackballs, printers, card readers, scanners (such as barcode, fingerprint, iris, QR code, and other types of scanners), RFID devices, tape drives, touch screens, cameras, movement sensors, network cards, storage devices, microphones, audio speakers, styli and transducers, and associated interfaces and drivers.

"Memory" may comprise any computer readable medium in which information can be temporarily or permanently stored and retrieved. Examples of memory include various types of RAM and ROM, such as SRAM, DRAM, Z-RAM, flash, optical disks, magnetic tape, punch cards, EEPROM, and combinations thereof. Memory may be virtualized, and may be provided in or across one or more devices and/or geographic locations, such as RAID technology, for example.

"Network" may comprise a cellular network, the Internet, intranet, local area network (LAN), wide area network (WAN), Metropolitan Area Network (MAN), other types of area networks, cable television network, satellite network, telephone network, public networks, private networks, wired or wireless networks, virtual, switched, routed, fully connected, and any combination and subnetwork thereof. A network may use a variety of network devices, such as routers, bridges, switches, hubs, repeaters, converters, receivers, proxies, firewalls, translators and the like. Network connections may be wired or wireless, and may use multiplexers, network interface cards, modems, ISDN terminal adapters, line drivers, and the like. A network may comprise any suitable topology, such as point-to-point, bus, star, tree, mesh, ring, and any combination or hybrid thereof.

"Program" may comprise any sequence of instructions, such as an algorithm, for example, whether in a form that can be executed by a computer (object code), in a form that can be read by humans (source code), or otherwise. A program may comprise or call one or more data structures and variables. A program may be embodied in hardware, software, firmware, or a combination thereof. A program may be created using any suitable programming language, such as C, C++, Java, Perl, PHP, Ruby, SQL, other languages, and combinations thereof. Computer software may comprise one or more programs and related data. Examples of computer software may include system software (such as operating system software, device drivers and utilities), middleware (such as web servers, data access software and enterprise messaging software), application software (such as databases, video games and media players), firmware (such as software installed on calculators, keyboards and mobile phones), and programming tools (such as debuggers, compilers and text editors).

"Signal" means a detectable physical phenomenon that is capable of conveying information. A signal may include but is not limited to an electrical signal, an electromagnetic signal, an optical signal, an acoustic signal, or a combination thereof.

The invention claimed is:

1. A computer-assisted patient navigation and communication system that receives communications from a patient regarding the patient's symptoms, scans patient data to determine the medical needs of the patient, and displays information to navigation personnel who can immediately navigate the patient to the most appropriate medical provider and/or service responding to the patient's identified symptoms, said system comprising:
   a) a call center having said navigation personnel who navigate the patient to the most appropriate response by either (i) providing assessment, diagnosis, treatment, and/or education to said patient, or (ii) further navigating the patient to the most appropriate medical provider inside or outside the call center for assessing, diagnosing and/or treating the patient's symptoms; and
   b) said call center having facilities for communications between said patient and said navigation personnel, said facilities being arranged and configured for receiving, recording and displaying patient physiological data from one or more of the following sources: patient's oral or electronic communications, patient's video communications, physiological monitors possessed by the patient, patient physiological monitors located at remote facilities, patient physiological data in the patient's electronic health records, and/or data obtained from health care personnel associated with the patient;
   c) wherein said communications and patient physiological data enable said navigation personnel to assess, diagnose, treat, educate and/or refer said patient to one or more of the following medical providers: a laboratory, imaging facility, pharmacy, home health personnel, physical therapist, ambulance facility, hospital, emergency room, physician and/or medical specialist responding to the patient's identified symptoms.

2. The system according to claim 1, wherein personnel qualifications of said navigation personnel and said medical providers are input in the system and associated with patient symptoms, patient chronic diseases and/or patient communication barriers.

3. The system according to claim 2, wherein personnel qualifications of each navigation personnel and medical provider include one or more of the following: credentials, areas of special knowledge, and languages spoken.

4. The system according to claim 3, further comprising algorithms for first verifying the correctness of the incoming patient physiological data, and then weighting the patient communications and patient physiological data, and associating certain navigation personnel and medical providers with specific conditions and symptoms.

5. The system according to claim 1, wherein said navigation personnel consist of health care providers defined as physicians, physician assistants or nurses.

6. The system according to claim 1, wherein said call center is a virtual call center.

7. A virtual medical system for minimizing anxiety of a patient with health symptoms, said system designed to speedily navigate the patient to the most appropriate medical provider and/or service most responsive to the patient's health symptoms, said system to include:
   a) a computer-assisted patient navigation and communication system that receives communications from the patient regarding the patient's symptoms, receives and scans patient physiological data to further determine the medical needs of the patient, and displays information to navigation personnel who speedily navigate the patient to the most appropriate service or medical provider responding to the patient's identified symptoms;
   b) wherein said system includes a call center having said navigation personnel who navigate the patient to the most appropriate service responding to the patient's identified symptoms by either (i) providing assessment, diagnosis, treatment, and/or education to said patient, or (ii) further navigating the patient to the most appropriate medical provider inside or outside the call center for further assessment, diagnosis and/or treatment of the patient's symptoms.

8. The system according to claim 7, wherein said call center has facilities for communications between said patient and said navigation personnel, said facilities being arranged and configured for receiving, recording and displaying said patient physiological data from one or more of the following sources: patient's oral communications, patient's electronic communications, patient's video communications, physiological monitors possessed by the patient, patient physiological monitors located at remote facilities, patient physiological data in the patient's electronic health records, and/or data obtained from health care personnel associated with the patient; wherein said communications and said patient physiological data enable said navigation personnel to assess, diagnose, treat, educate, and/or refer said patient to one or more of the following: a laboratory, imaging facility, pharmacy, home health personnel, physical therapist, ambulance facility, hospital, emergency room, physician and/or medical specialist responding to the patient's identified symptoms.

9. The system according to claim 8, wherein said remote facilities include prisons, business institutions, nursing homes, rehabilitation centers, managed care organizations and their enrolled personnel, and medical clinics.

10. The system according to claim 7, wherein said call center is provided with computer facilities having data algorithms for scanning said patient physiological data and patient communications for abnormal physical and physiological effects and for informing said navigation personnel of said abnormal physical and physiological effects.

11. The system according to claim 10, wherein said patient physiological data can be automatically received and timely scanned with algorithms to identify adverse physiological data selected from the following groups: adverse blood sugar, abnormal oxygen saturation, abnormal heart physiological data and abnormal blood pressure.

12. The system according to claim 11, wherein said system is provided with automated patient engagements, communications and interactions relating to said adverse physiological data.

13. A computer-assisted patient navigation and communication system for immediate determination of a remotely-monitored patient's medical needs and for guidance of the patient to the most appropriate medical provider and/or service responsive to the patient's symptoms, said system comprising:
  a) an external system interface configured for receiving patient physiological data from one or more of the following sources: patient's oral communications, patient's electronic communications, patient's video communications, physiological monitors possessed by the patient, patient physiological monitors located at remote facilities, patient physiological data in the patient's electronic health records, and/or data obtained from health care personnel associated with the patient;
  b) an enablement system configured for analyzing said patient physiological data and transferring information pertaining to said physiological data to navigation personnel associated with a navigation station of said system;
  c) an internal system interface configured for providing said patient data to said navigation personnel; and
  d) said navigation station configured for inbound and outbound oral, data and/or video communications between or among two or more of the following: the patient, the navigation personnel, and the medical provider, wherein said medical provider is defined as a laboratory, imaging facility, pharmacy, home health personnel, physical therapist, ambulance facility, hospital, emergency room, physician, and/or medical specialist.

14. The system according to claim 13, wherein said navigation personnel consist of health care providers, which include physicians, physician assistants, and nurses.

15. The system according to claim 13, wherein said external system interface formats said patient physiological data in a prescribed format to form EMR data.

16. The system according to claim 15, wherein said enablement system is configured for analyzing said EMR data, identifying an abnormality, and transferring information relating to said abnormality to said navigation personnel.

17. The system according to claim 13, wherein said physiological data is received from a voice or keypad entry on said patient's phone.

18. The system according to claim 13, wherein said patient is guided to the most appropriate medical provider responsive to the patient's symptoms by using an enablement system that inputs in the system personnel qualifications of said navigation personnel and said medical providers, wherein said enablement system associates said personnel qualifications with patient symptoms, patient chronic diseases and/or patient communication barriers.

19. The system according to claim 18, wherein personnel qualifications of each navigation personnel and medical provider include one or more of the following: credentials, areas of special knowledge, and languages spoken.

20. The system according to claim 19, further comprising algorithms for first verifying the correctness of the incoming patient physiological data, and then weighting the patient communications and patient physiological data, and associating certain navigation personnel and medical providers with specific conditions and symptoms.

* * * * *